US007854922B2

(12) United States Patent
Tanabe et al.

(10) Patent No.: US 7,854,922 B2
(45) Date of Patent: Dec. 21, 2010

(54) SKIN PREPARATION FOR EXTERNAL USE CHARACTERIZED BY CONTAINING SUGAR DERIVATIVE OF α, α-TREHALOSE

(75) Inventors: Fujimi Tanabe, Okayama (JP); Michio Kubota, Okayama (JP); Hiromi Tatsukawa, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 689 days.

(21) Appl. No.: 10/545,166

(22) PCT Filed: Feb. 10, 2004

(86) PCT No.: PCT/JP2004/001401

§ 371 (c)(1), (2), (4) Date: Aug. 11, 2005

(87) PCT Pub. No.: WO2004/071472

PCT Pub. Date: Aug. 26, 2004

(65) Prior Publication Data

US 2007/0003502 A1 Jan. 4, 2007

(30) Foreign Application Priority Data

Feb. 13, 2003 (JP) ............................ 2003-035751
Aug. 29, 2003 (JP) ............................ 2003-305821

(51) Int. Cl.
*A61K 8/73* (2006.01)
*A61K 36/00* (2006.01)
*A61K 31/715* (2006.01)
*A61K 31/70* (2006.01)
*A61K 31/728* (2006.01)

(52) U.S. Cl. ...................... 424/70.13; 424/725; 514/27; 514/33; 514/53

(58) Field of Classification Search ................. 424/401, 424/70.13, 725; 514/27, 33, 53
See application file for complete search history.

(56) References Cited

U.S. PATENT DOCUMENTS 4,839,164 A * 6/1989 Smith .......................... 424/64
5,714,368 A * 2/1998 Nakada et al. .............. 435/201

OTHER PUBLICATIONS

Vitamin A/Retinyl Palmitate [online]. Dermaxine, 2005 [retrieved on Feb. 5, 2010]. Retrieved from the Internet: <URL: http://web.archive.org/web/20050616083632/http://www.dermaxime.com/vitamin-a.htm>.*

Hyaluronic Acid for Skin Hydration and Possibly a Lot More, [online]. Smart Skin Care.comCorporation, 1999 [retrieved on Feb. 5, 2010]. Retrieved from the Internet: <URL:http://www.smartskincare.com/treatments/topical/hyaluronic-acid.html>.*

Hyaluronic Acid Definition, Dead Sea Cosmetics Ingredient FAQS [online]. Dead Sea Cosmetics, 2002 [retrieved on Feb. 5, 2010]. Retrieved from the Internet: <URL:http://web.archive.org/web/20020204151335/http://deadsea-cosmetics.com/ingrediantsnew.htm>, pp. 1 and 6.*

* cited by examiner

*Primary Examiner*—Johann R Richter
*Assistant Examiner*—Andriae M Holt
(74) *Attorney, Agent, or Firm*—Browdy and Neimark, PLLC

(57) ABSTRACT

The present invention has an object to provide an external dermatological formulation having satisfactory blood flow-promoting effect, antiinflammatory effect, antibacterial effect, moisturizing effect, whitening effect, UV-absorbing effect, UV-scattering effect, antioxidant effect, hair growing effect, hair nourishing effect, emusifying effect, astringent effect, wrinkle-reducing effect, cell-activating effect and/or transdermal absorption-promoting effect with a satisfactory safety and skin feeling; The object is solved by providing an external dermatological formulation comprising a saccharide derivative of α,α-trehalose and one or more members selected from substances having any one of blood flow-promoting effect, antiinflammatory effect, antibacterial effect, moisturizing effect, whitening effect, UV-absorbing effect, UV-scattering effect, antioxidant effect, hair growing efect, hair nourishing effect, emulsifying effect, astringent effect, wrinkle-reducing effect, cell-activating effect and transdermal absorption-promoting effect.

4 Claims, No Drawings

SKIN PREPARATION FOR EXTERNAL USE CHARACTERIZED BY CONTAINING SUGAR DERIVATIVE OF α, α-TREHALOSE

TECHNICAL FIELD

The present invention is to provide an external dermatological formulation, which comprises a saccharide derivative of α,α-trehalose and one or more members selected from substances having any one of blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect; and to provide an external dermatological formulation which has a comfortable feeling, enhanced above effects, and insubstantial sticky feeling.

BACKGROUND ART

The skins including the head skin may have troubles such as a rough skin, suntan, aging, liver spot, wrinkle and loss of hair due to internal or external factors or aging. Many of these troubles are accompanied by poor blood circulation and/or inflammation in the part or whole of the skins. To solve such problems, usual external dermatological formulations have been used in combination with a synthetic drug or natural extract having blood flow-promoting effect, antiinflammatory effect, antibacterial effect, moisturizing effect, whitening effect, UV-absorbing effect, UV-scattering effect, antioxidant effect, astringent effect, wrinkle-reducing effect, cell-activating effect or transdermal absorption-promoting effect. However, such ingredients may not exert the desired effects when used alone or in a low dose. While, when used in a high dose, they may cause irritating feeling, unpleasant smell, insufficient extension and sticky feeling in the skins. Further, when continuously used, they may cause the dermatitis and rough skin.

To solve these problems, Japanese Patent Publication (Kokai) No. 128,136/94 discloses an external dermatological formulation enhanced in the antiinflammatory effect, which contains α,α-trehalose and substance having an antiinflammatory effect or blood flow-promoting effect. Japanese Patent Publication (Kokai) No. 77,650/97 discloses a cosmetic having a satisfactory spreading property without causing/inducing sticky feeling, which contains trehalose, monosaccharides or sugar alcohols thereof, and disaccharides or sugar alcohols thereof. The present applicant disclosed an applicability of α,α-trehalose or saccharide derivatives thereof for cosmetics in Japanese Patent Publication (Kokai) Nos. 143,876/95, 73,504/96 and 228,980/2000, and Japanese Patent No. 3,182,679. However, these patent literatures never disclose any evidence that saccharide derivatives of α,α-trehalose inhibits the reduction of uncomfortable feelings such as sticky feeling, insufficient spreading property and irritating feeling caused by substances having any one of blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect. In addition, they never disclose concretely any evidence that saccharide derivatives of α,α-trehalose enhance the effects of ingredients applicable to external dermatological formulation. They never disclose that a saccharide mixture containing α-maltosyl α,α-trehalose and sugar alcohols as effective ingredients is more effective.

The present invention has an object to provide an external dermatological formulation having a satisfactory safety and comfortable feeling without sticky feeling, which is enhanced in one or more effects of the substances selected from those having blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect.

DISCLOSURE OF THE INVENTION

The present inventors have eagerly studied on use of saccharides to attain the above object. As a result, they revealed that saccharide derivatives of α,α-trehalose synergistically enhance the effects of ingredients for external dermatological formulation, such as substances having any one of blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect, without uncomfortable feeling such as sticky feeling, irritating feeling and uncomfortable spreading property. Particularly, they revealed that the saccharide derivatives of α,α-trehalose enhanced the substances having blood flow-promoting effect and/or antiinflammatory effect to prevent or improve rough skins, suntan, aging, liver spot, or wrinkle, and accomplished this invention. The present invention provides an external dermatological formulation, which is characterized in that it comprises substances having anyone of blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect or transdermal absorption-promoting effect, and it is enhanced in such effects. It also has a satisfactory feeling and safety without sticky feeling, irritating feeling and uncomfortable spreading property, and excellent effect on preventing or curing rough skin, sunburn, liver spot and wrinkle.

BEST MODE FOR CARRYING OUT THE INVENTION

The term "external dermatological formulation" as referred to as in the present invention means an agent to be directly applicable for the skins such as of the face and body, mucosae, hair and head skin of human, pets or domestic animals for the purpose of preventing the rough skin, suntan, liver spot, wrinkle, inflammation, or aging, curing various diseases such as atopic diseases, allergic diseases, ulcers, injures and infectious diseases, moisturizing, whitening, beauty treatment, hair nourishing or hair glowing. The above term includes cosmetics including skin-care cosmetics, makeup cosmetics, body-care cosmetics, hair-care cosmetics, oral-care cosmetics, and fragrance cosmetics, quasi-drugs and pharmaceuticals, which are illustrated with cosmetic soaps, facial soap, shampoo, rinse, hair shampoo, cosmetics for hair, usual cream/milky lotions, cream for shaving, cosmetic lotions, eau de cologne, lotion for shaving, cosmetic oils, face powders, foundations, cheek rouge, eyebrow pencil, eye cream, eye shadow, mascara, perfume, sun cream, sun block cream, sun lotion, sun block lotion, sun oil, sun block oil, nail cream, enamel, enamel remover, eyeliner, lipstick, lip cream, toothpaste, bath cosmetics, or preparations for curing various diseases. In addition, it also includes quasi-drugs or pharmaceuticals used in an manner of applying or adhering on skins or mucosae, such as ointments, cataplasms and films, quasi-drugs or foods and beverages used orally such as oral refrigerant. Further, it also includes groceries possible to contact with and influence skins, such as soaps and detergents for washing, detergents for floors, cleansers, and detergents for kitchen.

The term "inflammation" as referred to as in the present invention means inflammatory changes in epidermis such as of the head skins, mucosae and skins, mainly, and includes redness of the skins due to slight degree of sunburn, stomatitis, acne, heat rash, rough and swelling of throat, itch, pain, generation of erythema, papule or bulla, generation of ulcer, and eczema. It properly involves stomatitis due to autoimmune diseases such as Sjögren's syndrome, clinical syndromes such as dry mouth due to the stamatitis, and inflammation and bleeding of teeth ridges due to alveolar pyorrhea. Such inflammations are sometimes caused by external stimulations and/or factors of living bodies (including constitutional factors), or in combination thereof. The external stimulations are illustrated with various chemical substances, cosmetics, metals, detergents or drugs, and further biological factors such as microorganisms, plants, animals and insects, and physical factors such as sunlight, heat, cold and dryness. The biological factors include other factors due to regional disorders such as sweating, secretion of sebum and keratosis, or systemic disorders such as atopic diseases, allergic diseases, infections, disorders in internal organs such as digestive organs, liver, or kidney. The inflammations properly include inflammations due to ingredients of external dermatological formulations.

The term "saccharide derivatives of α,α-trehalose" as referred to as in the present invention includes any one or more non-reducing oligosaccharides having the α,α-trehalose structure and composed of three or more glucose residues. The external dermatological formulation of the present invention comprises one or more such oligosaccharides. Concretely, these saccharide derivatives of α,α-trehalose are composed of one α,α-trehalose molecule and either of mono-glucose residue, di-glucose residue, tri-glucose residue or tetra-glucose residue bound to both or either end of the α,α-trehalose molecule. The saccharide derivatives of α,α-trehalose, preferably used in the present invention, are composed of three to six glucose residues as previously disclosed by the same applicant in Japanese Patent Publication (Kokai) Nos. 143,876/95, 73,504/96 and 228,980/00, and Japanese Patent No. 3,182,679. Such saccharide derivatives are illustrated with mono-glucosyl α,α-trehalose such as α-maltosyl α-glucoside and α-isomaltosyl α-glucoside; di-glucosyl α,α-trehalose such as α-maltotriosyl α-glucoside (alias α-maltosyl α,α-trehalose), α-maltosyl α-maltoside, α-isomaltosyl α-maltoside and α-isomaltosyl α-isomaltoside; tri-glucosyl α,α-trehalose such as α-maltotetraosyl α-glucoside (alias α-maltotriosyl α,α-trehalose), α-maltosyl α-maltotrioside, α-panosyl α-maltoside; and tetra-glucosyl α,α-trehalose such as α-maltopentaosyl α-glucoside (alias α-maltotetraosyl α,α-trehalose), α-maltotriosyl α-maltotrioside and α-panosyl α-maltotrioside.

Such saccharide derivatives of α,α-trehalose can be produced by fermenting method, enzymatic method or organic synthetic method, and are never restricted to specific origin or process. For example, the saccharide derivatives can be directly prepared from starch materials or hydrolyzates thereof by the enzymatic methods disclosed by the same applicant in Japanese Patent Publication (Kokai) Nos. 143,876/95, 73,504/96 and 228,980/00, and Japanese Patent No. 3,182,679. In addition, they can be prepared by reacting starch hydrolyzates rich in some kinds of oligosaccharides such as maltotetraose, maltopentaose, maltohexaose and maltoheptaose obtainable with a maltotetraose producing enzyme disclosed in Japanese Patent Publication (Kokai) No. 143,876/95, an α-amylase capable of efficiently producing maltopentaose disclosed in Japanese Patent Publication (Kokoku) No. 14,962/95 and a maltohexaose maltoheptaose producing amylase disclosed in Japanese Patent Publication (Kokai) No. 236,478/95 with non-reducing saccharide producing enzyme disclosed in Japanese Patent Publication (Kokai) No. 143,876/95. Further, they can be prepared by reacting a solution containing starch or hydrolyzates thereof and α,α-trehalose with an enzyme capable of transferring glycosyl group such as cyclodextrin glucanotransferase. The resulting reaction mixture obtained by the above method can be used as a saccharide solution containing saccharide derivatives of α,α-trehalose. Optionally, they can be partially or highly purified. Such preparation processes, using easily and cheaply available starch materials, are advantageously used in view of industrial production because of their sufficient production yield and low cost.

When applied to subjects, the saccharide derivatives having a trehalose structure at the end of the molecules more effectively improve skin feeling and enhances the blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect, and has strong moisturizing property among the saccharide derivatives of α,α-trehalose described above. Particularly, saccharide mixtures containing α-maltotriosyl α-glucoside (alias α-maltosyl α,α-trehalose) as a main ingredient and one or more saccharides selected from the group consisting of α-maltotriosyl α-glucoside (alias α-glucosyl α,α-trehalose), α-maltotetraosyl α-glucoside (alias α-maltotriosyl α,α-trehalose), and α-glucosyl α-glucosides other than the saccharide derivatives of α,α-trehalose described above. The amount of α-maltosyl α,α-trehalose in each of the saccharide mixtures is 5% by weight or more (hereinafter, "% by weight" is simply represented by "%"), preferably 10% or more, more preferably 20% or more, and most preferably 50% or more.

Among the above saccharides, α-maltosyl α-glucoside and α-maltotetraosyl α-glucoside in a crystalline form are disclosed in Japanese Patent No. 3,182,679 and Japanese Patent Publication (Kokai) No. 228,980/00. To exert the desired effect according to this invention, such crystalline saccharides are preferably used after changed into amorphous states such as liquid states, syrupy states, and glassy paste or solid states. α-Maltotetraosyl α-glucoside, as one of the easily crystallized saccharide derivatives of α,α-trehalose, can be used for toothpaste as an abrasive with a low hardness after partially or completely formed in a crystal. In addition, it also can be used as a UV-scattering agent for sun-protect and as a base ingredient for finishing cosmetics such as eye shadow, mascara, or foundation with stabilizing function for colorants in an external dermatological formulation.

As described above, the saccharide derivatives of α,α-trehalose used in the present invention are preferable in an amorphous state. It can be used in any form such as syrup, masquitte, paste, powder, solid, granule and tablet as long as it contains one in an amorphous form. If necessary, they can be used in combination with fillers, excipients or binders.

The saccharide derivatives of α,α-trehalose can be incorporated into the formulation of the present invention at a desired processing step from processing of raw materials before obtaining the final products by conventional methods. Examples of such methods are mixing, kneading, resolving, melting, dispersing, suspending, emulsifying, forming inverse micelle, penetrating, crystallizing, scattering, applying, spraying, injecting, immersing, solidifying and holding.

The amount of saccharide derivatives of α,α-trehalose in the formulation of the present invention is not specifically restricted as long as it is enough to be capable of enhancing any one of blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect. It is usually about 0.01% or more, preferably about 0.1% or more, more preferably about 0.2% or more to the weight of a final product, on a dry solid basis. Usually, in the case of less than about 0.01%, it is insufficient to enhance the effects by these substances even when used in combination with one or more substances. The upper limit of the amount of the saccharide derivatives of α,α-trehalose is not specifically restricted as long as they do not affect the quality and function of objective external dermatological formulations.

The saccharide derivatives of α,α-trehalose can be incorporated alone into the formulation of the present invention. Optionally, a saccharide mixture, containing other saccharides and/or sugar alcohols together with the saccharide derivatives of α,α-trehalose (hereinafter, it is described as "saccharide mixture containing saccharide derivatives of α,α-trehalose"), can be used. Examples of such other saccharides are glucose, isomaltose, maltose, oligosaccharide and dextrin, which are produced from starch materials in the preparation of the saccharide derivatives of α,α-trehalose. Particularly, the saccharide mixture containing sugar alcohols together with saccharide derivatives of α,α-trehalose produced by hydrogenating a saccharide mixture containing reducing saccharides together with saccharide derivatives of α,α-trehalose to convert the reducing saccharide into sugar alcohols, has a satisfactory moisturizing effect and a moderate viscosity, and inhibits sticky feeling of external dermatological formulations, improves skin feeling, and imparts gross in the skins and hairs. When applied to the skins, it gives a satisfactory skin feeling differing from conventional base cosmetics containing glycerin. In addition, it is effective on improving the holding property of cosmetics including moisturizing property. Particularly, a saccharide mixture, containing 20% or more, preferably 50% or more, more preferably 50-70% of α-maltosyl α,α-trehalose; 5-25% of total other saccharide derivatives of α,α-trehalose; 5-45%, preferably 25-45% of sugar alcohols selected from sorbitol and sugar alcohols of maltooligosaccharides, is preferable in view of enhancing the effect of other ingredients and showing satisfactory moisturizing effect and skin feeling. Maltitol, maltotriitol and/or maltotetraitol are more preferable among sugar alcohols of maltooligosaccharides.

The saccharide derivatives of α,α-trehalose also have a cell-protecting effect against external stress such as heat, UV and dryness, and also have a cell-activating effect. Therefore, they improve the metabolism of the skins, mucosae or head skins damaged by UV or other factors or suffered from roughness or inflammation, when used alone or as ingredient for an external dermatologic formulation. Further, they inhibit the roughness, aging and inflammation and promote the recovery for the normal skins, mucosae or head skins by inhibiting the production of inflammatory cytokines including tumor necrosis factor (hereinafter, designated as "TNF-α") and interleukin-1 and the expression of intercellular adhesion molecules. Furthermore, they lower the irritations due to various ingredients contained in the external dermatologic formulation and physical irritations when applied to the skins. Therefore, the external dermatological formulation of the present invention can be advantageously used even if applied to a painful skin, including the skins, mucosae or head skins, which are suffered from inflammation due to sunburn or other disorders. The saccharide derivatives of α,α-trehalose of the present invention make the skins or hairs smooth in such a manner of coating surface of the skins, mucosae or hairs. They also impart soft feelings and textures thereof, strengthen barrier function thereof and protect surface of skins or cuticle on surfaces of damaged hair. In addition, they have an antielectrostatic effect. Therefore, they can be advantageously used as a protectant for the hairs, hair roots, head skins, skins or mucosae; a smoothing agent; a gross imparting agent; a conditioning agent; an antielectrostatic agent; or a base, for hair-coloring agent. The saccharide derivatives of α,α-trehalose or saccharide mixture containing the same are soluble in various substances used in external dermatological formulations such as emulsifiers described below, solvents including ethanol, 1,3-butylene glycol, propylene glycol, concentrated glycerin, dipropylene glycol or 1,2-pentanediol, polyols including sorbitol or maltitol, and synthetic polymers including polyethylene glycol (molecular weight 400-6,000) or carboxyvinylpolymer. They enable to prepare more homogenous and fine emulsified particles when used in creams with substances having emulsifying effect compared with the use of glycerin alone because they effectively reduce surface tension without forming a milkiness and a precipitation in spite of a lower solvent activity than glycerin. When used in a cleansing foam, shampoo or rinse, they impart elasticity to the produced foam, increase the production of foam, retain the produced foam, the saccharide derivatives of α,α-trehalose inhibit physical stimulation of the produced foam against the skins. Therefore, the external dermatological formulations containing them are used for cleaning the skins easily and comfortably, and are capable of clearly removing dirt from inner pores with dense forms and giving both of clear feeling and moisture to the skins after application. The saccharide derivatives of α,α-trehalose or saccharide mixture containing the same of the present invention have the effects on the inhibition of the oxidation and/or deterioration of lipids, or the stabilization and antioxidation of lipid membranes of liposomes or cells. In addition, since they inhibit the oxidation, decomposition, browning or discoloration of various substances acceptable for external dermatological formulations as well as the generation of foreign tastes and foreign smells, they are useful for external dermatological formulations containing substances easily oxidized, browned, or discolored. Examples of such substances are substances having emulsifying effect such as amino acid type detergents; colorants such as natural colorants and synthetic colorants; perfumeries such as floral perfumeries; ascorbic acid; ascorbic acid 2-glucoside; tannin liquids; honey; beeswax; propolis; and amino acids. Therefore, they are used as ingredients for external dermatological formulations without sticky feeling, which can be advantageously used as moisturizing agent, moisture controlling agent, quality keeping agent, cell-protecting agent, cell-activating agent, foam-quality improving agent, foam-quality controlling agent, stabilizer, browning inhibitory agent, discoloration inhibitory agent, antioxidant for lipids, aroma-retaining agent.

The saccharide derivatives of α,α-trehalose of the present invention have no irritation and a high safety. They are hardly assimilated by anaerobitic resident bacteria in the skins or mouths, such as *Lactobacilus pentosus, Propionibacterium acnes* and *Streptococcus mutans*. Therefore, they can be advantageously used as ingredients for an external dermatological formulation in order to treat bacterial skin disorders such as acnes, or used as toothpaste.

Any quality or quantity of substances, having blood flow-promoting effect, antiinflammatory effect, antibacterial effect, moisturizing effect, whitening effect, UV-absorbing effect, UV-scattering effect, antioxidant effect, hair growing and hair nourishing effect, astringent effect, wrinkle-reducing effect, cell-activating effect or transdermal absorption-promoting effect, can be used for the external dermatological formulation of the present invention as long as they do not affect the desired effects. According to desired use, they can be used alone or in combination with two or more substances. If necessary, two or more substances having the same effect can be used in combination.

Examples of such substances having blood flow-promoting effect are plant or plant ingredients such as sialid, ginseng, ginkgo, ginger, garlic, angelica, arnica, fennel, plectranthi herba, *Nasturtium officinale*, chamomile, Roman chamomile, carrot, gentian, burdock, rice, crataegi fructus, "shiitake", *Crataegus oxyacantha*, juniper, *Cnidium rhizome*, thyme, clove, citrus unshiu peel, Japanese angelica root, persicae semen, *Paulownia bark*, butche's broom, grape, peony, horse chestnut, balm mint, *Citrus junos*, coix seed, rosemary, rose hips, citrus unshiu peel, Japanese angelica, peach, apricot, walnut, horsetail, calamus root, aloe, Plectranthi herba, gentian, capsicum and *Citrus junos*, hesperetin, hesperidin, glycosyl hesperidin, quercetin, rutin, glycosyl rutin, naringenin, naringin, glycosyl naringin, esculetin, esculin, glycosyl esculin, acetylcholine, carpronium chloride, diphenhydramine hydrochloride, γ-oryzanol, 1-menthol, cepharanthine, vitamin E or vitamin E derivatives including d-δ-tocopherol, dl-α-tocopherol, dl-α-tocopherol acetate, dl-α-tocopherol linoleate, dl-α-tocopherol nicotinate, dl-α-tocopherol succinate and vitamin E nicotinate, minoxidil, nicotinamide, vanillylamide nonylate, carpronium chloride, or carbon dioxide. The amount of the substance is not specifically restricted as long as the saccharide derivatives of α,α-trehalose are capable of enhancing the effect of the above substances having blood flow-promoting effect alone or in combination with other ingredients. It is usually 0.001-5%, preferably 0.01-2% to the total amount of the external dermatological formulation. In the case of less than 0.001%, they are not expected to exert the desired effect. In the case of more than 5%, they are not dose-dependently effective. When used in a hair tonic containing these substances as effective ingredients, the amount of the substances is not specifically restricted as long as the saccharide derivatives enhance the hair-growing effect, and it is usually 0.0001-5%, preferably 0.002-3%. The term "plant or plant ingredient" as referred to as in the present invention means crushed materials from plant bodies such as leaves, stems, roots, flowers, fruits and bark; and extracts such as of essential oils, oils, fats and tinctures, obtained by treating with water, methanol, ethanol, ether, ethyl acetate, acetone or butylene glycol form plant materials. The resulting materials are optionally purified roughly or completely. The term "substances having blood flow-promoting effect" as referred to as in the present invention includes substances having the effect on expanding the blood vessels to promote blood circulation. In addition, it also includes substances having the effect on inducing a factor having blood flow-promoting effect with a local administration. Examples of such substances are capsoci tincture, zingiberis tincture, kantiris tincture and wanyl norylate.

The term "substances having antiinflammatory effect" as referred to as in the present invention includes allantoin or derivatives thereof such as allantoin acetyl-dl-methionine, allantoin chlorhydroxy aluminum, allantoin dihydroxy aluminum or allantoin polygalacturonate; glycyrrhetin or derivatives thereof such as glycyrrhetinic acid, glycyrrhizinic acid, allantoin glycyrrhetinate, glycerin glycyrrhetinate, stearyl glycyrrhetinate, glycyrrhetinyl stearate, disodium 3-succinyloxyglycyrrhetinate, dipotassium glycyrrhizinate, monoammonium glycyrrhizinate; pantothenic acid or derivatives thereof such as pantothenic acid, pantothenyl alcohols, pantothenyl ethyl ethers, acetyl pantothenyl ethyl ethers, benzoilpantothenylethyl ethers, calciumpantothenate, sodium pantothenate, acetyl pantothenyl ethyl ethers, pantothenyl ethyl ether benzoate, and pantethine; vitamin E or derivatives thereof such as vitamin E, d-δ-tocopherol, dl-α-tocopherol, dl-α-tocopherol acetate, dl-α-tocopherol linoleate, dl-α-tocopherol nicotinate, and dl-α-tocopherol succinate; L-ascorbic acid or derivatives thereof such as L-ascorbic acid, L-ascorbic acid glycoside including L-ascorbic acid 2-glucoside, acyl derivatives of L-ascorbic acid glycoside, ascorbyl tetrahexyldeconate, ascorbic acid tocopherol phosphate diesthers, L-ascorbic acid sulfate esthers, ascorbyl dipalmitate, ascorbyl palmitate, stearyl L-ascorbate, L-ascorbyl phosphate, ethyl L-ascorbate, acyl derivatives, alkali metal or alkaline earth metal salts thereof; pyridoxine hydrochloride; menthol; biotin; camphor; turpentine; zinc oxide; azulene; guaiazulene and derivatives thereof; mefenamic acid or derivatives thereof; phenylbutazone or derivatives thereof; indomethacin or derivatives thereof; ibuprofen or derivatives thereof; ketoprofen or derivatives thereof; ϵ-aminocapronic acid; sodium diclofenac; diphenhydramine; tranexamic acid or derivatives thereof; dexamethasone; cortisone or esthers thereof; hydrocortisone or esthers thereof; adrenal cortical hormone such as prednisone and prednisolone; antihistamic agent; rose fruit; *Bistorta Major*; turmeric; *Hypericum erectum*; phellodendron bark; glycyrrhiza; *Lonicera japonica*; watercress; comfrey; acanthopanacis bark; sage; lithospermum root; white birch; tea leaf; tian cha; *Calendula officinatis*; elderberry; *Typha angustifolia; Sapindus mukurossi*, eucalyptus extract, broccoli, Japanese angelica root, loquat, labiate, chamomile, wormwood, aloe, ginseng, indigo, phellodendron bark powder, *Myrica rubra* bark, gambir, sweet hydrangea leaf, *Althea officinalis* root, arnica, echinacea, Plectranthi herba, scutellaria root, barley, St. John's wort, orange, Japanese valerian, Roman chamomile, *Artemisia caplillaris*, cucumber, gardenia, *Sasa albo-marginate*, gentian, geranium herb, burdock, *Xanthoxylum piperitum*, linden, peony root, ivy, juniper, peppermint, *Cnidium rhizome*, sialid, sage, mori cortex, jujube, thyme, rose hips, *Benincasae semen, Calendula officinalis*, persicae semen, houttuynia, cordata, *Potantilla tormentilla*, parsley, mint, nettle, sandalwood, Butcher's bloom, grape, safflower, peony, linden, horse chestnut, peach, cornflower, wormwood, lavender, rosemary, carrot and Japanese angelica root. The amount of the substances is not specifically restricted as long as the saccharide derivatives of α,α-trehalose are capable of enhancing the effect of the above substances having antiinflammatory effect against dermatitis alone or in combination with other ingredient. It is usually 0.001-5%, preferably 0.01-3% to the total amount of the external dermatological formulation. In the case of less than 0.001%, they are expected to exert the desired effect. In the case of more than 5%, they are not dose-dependently effective. When the ingredients are known to be in plant tissues, for example, glycyrrhizin in glycyrrhiza, they are properly prepared as extracts of plants containing thereof to be added to the present formulation.

The external dermatological formulation of the present invention contains one or more substances having any one of antibacterial effect, moisturizing effect, whitening effect, UV-absorbing effect, UV-scattering effect, antioxidant effect, hair growting efect, hair nourishing effect, astringent effect, wrinkle-reducing effect, cell-activating effect and transdermal absorption-promoting effect as well as the above substances having blood flow-promoting effect and/or antiinflammatory effect. It can contain these substances together with the above substances. Optionally, it contains two or more substances having the same effect or physical property.

The term "substances having anti-bacterial effect" is not specifically restricted and can be selected from substances having antibacterial effect acceptable to external dermatological formulations substances having antibacterial effect. Example of such substances are lower alcohols such as ethanol; benzoic acid or salts thereof; benzoic acid esters; alkyl diaminoglycine hydrochloride; photosensitizing dye such as pionin (Kanko-so No. 201); chlorcresol; chlorbutanol; salicylic acid or salts thereof; sorbinic acid or salts thereof; sorbinic acid esters; dehydroacetate or salts thereof; trichlorohydroxy phenyl ethers; paraoxy benzoic esthers; sodium paraoxy benzoate; phenoxy ethanol; phenol; sodium rauryl aminoethyl glycine; resorcin; zinc-ammonia-silver substitutional zeolite; pantothenyl ethyl ethyl benzoate; isopropyl methyl phenol; cetylpyridium chloride; benzalkonium chloride; benzethonium chloride; chlorhexidine hydrochloride; orthophenyl phenol; sodium orthophenyl phenoxide; chlorhexidine gluconate, cresol, chloramine-T, chlorxylenol, chlorphenesin, chlorhexidine, 1,3-dimethylol-5,5-dimethlhydantoin, alkyl isoquinoliniumbromide, thianthol, thymol, trichloro carbanilide, parachlorphenol, halocarban, hinokithiol, zinc pyrithione, methyl chloroisothiazolinon/methlisothiazolin solution, N,N"-methylene bis[N'-(hydroxymethyl-2,5-dioxy-4-imidazolinyl)urea], 2-(p-dimethyl aminostyryl)-3-heptyl-4-metyl-thiazolinium iodide, imidazolidinyl urea, dimethylol dimethyl hydantoin, glutaraldehyde, jamal II, bisabolol, chlorhexidine gluconate, isopropyl methyl phenol, phenoxy ethanol, or plants or components thereof having an antibacterial effect such as hinokithiol, tea oil, propolis, *Sapindus mukurossi*, asparagus, aloe, gingko, turmeric, echinacea, Plectranthi herba, *Scutellaria radix, Coptis rhizome, Hypericum erectum*, clusiaceous, orange, *Artemisia capillaris*, gardenia, *Sasa albo-marginate, Sophora angustifolia*, grapefruit, *Geranium thunbergii, Xanthoxylum piperitum*, lithospermum root, labiate, white birch, *Lonicera japonica, Achillea millefolium*, peppermint, *Cnidium rhizome*, sage, mori cortex, thyme, clove, *Calendula officinalis*, peony, hop, mint, peach, eucalyptus, lavender, rose hips, rosemary, wormwood, peony root, calamus and *Saponaria officinalis*. The amount of the substances is not specifically restricted as long as the saccharide derivatives of α,α-trehalose are capable of enhancing the effect of the above substances having antibacterial effect alone or in combination with other ingredients. It is usually 0.0001-3% to total amount of the external dermatological formulation. In the case of less than 0.0001%, they are expected to exert the desired effect. In the case of more than 2%, they are not dose-dependently effective.

The term "substances having moisturizing effect" as referred to as in the present invention includes mucopolysaccharides or derivatives thereof and salts thereof such as hyaluronic acid, chondroitin sulfate, delmatan sulfate, heparan sulfate and heparin; ceramide; peptides, proteins or hydrolyzates thereof such as collagen, elastin, fibronectin, keratin, gelatin and casein; amino acids or derivatives thereof such as glycine, alanine, valine, serine, threonine, methionine, phenylalanine, leucine, tyrosine, proline, isoleucine, tryptphan, hydroxyproline, theanine, ornithine, citrulline, asparagine, aspartic acid, glutamine, glutamic acid, arginine, histidine, lysine, hydroxylysine, cysteine, cystine, acyl glutamate and γ-polyglutamic acid; pyrrolidone carbonate; pearl essence; reducing or non-reducing saccharides such as powder starch hydrolyzates, xylose, glucose, fractose, maltose, sucrose, lactose, paratinose, α,α-trehalose, α,β-trehalose (neotrehalose), β,β-trehalose (isotrehalose), isomerized sugar, honey, maple sugar, brown sugar, glycosyl sucrose-containing syrup, maltooligosaccharide, dextrin, isomaltooligosaccharide, galactooligosaccharide, fractooligosaccharide, nigerooligosaccharidel, galactosyl glucoside, lactosucrose, cyclic tetrasaccharide and/or derivatives thereof disclosed by the present applicant in International Patent Publication Nos. WO02/24,832, WO02/10361 and WO02/072594 and Japanese Patent Application No. 305,821/2000 specification, and starch; sugar alcohols such as erythritol, pentaerythritol, sorbitol, xylitol, maltitol, isomaltitol, lactitol and panitol; gums such as pullulan, levan, sodium arginate, agar, gum Arabic, guar gum, tragacanth gum, xanthane gum, carrageenan and locust bean gum; water-soluble polymers such as pectin, methyl cellulose, carboxy methyl cellulose, polyvinyl alcohol, polyvinyl pyrrolidone, polydextrose and polyacrylic acid; polyols such as sugar esthers, dextrin derivatives, glycerin, 1,3-butylene glycol, 1,4-butylene glycol, dipropylene glycol, polyethylene glycol, propylene glycol and amylene glycol; seaweeds such as coralline; plants or extracts thereof having moisturizing effect such as aloe, hamamelis, *Xanthoxylum piperitum, Artemisia vulgaris*, kava-kava, Asian ginseng, aloe, nettle, fennel, witch hazel, turmeric, *Lotus corniculatus, Phellodendron amurense, Hypericum erectum*, rice, chamomile, *Artemisia capillaris*, kiwi, cucumber, *Sophora angustifolia*, grape, gardenia, comfrey, *Saponaria officinalis*, rehmannia root, labiate, peony root, white birch, horsetail, linden, sage, sialid, *Cnidium rhizome*, mulberry, soybean, thyme, Japanese angelica root, *Calendula officinalis*, parsley, coix seed, Butcher's bloom, loofah, hop, horse chestnut, balm mint, peach, saxifrage, bramble, lavender, *Astragalus sinicus*, rose, *Rose multiflora*, rosemary, glycyrrhiza, tea leaf (green tea, black tea, oolong tea), lily, barley, wheat, apricot, oat, lithospermum root, lemon, quince, orange, strawberry, safflower, gentian, mint, spearmint, peppermint, *Sapindus mukurossi*, eucalyptus, *Lamium album*, pine, cornflower, *Sanguisorba officinalis*, avocado, seaweed, grapefruit, prune, lime, *Citrus iunos, Coptis rhizome*, cypress, peony, olive, sunflower, jojoba, macadamia nut, *Limnanthes alba*, camellia, almond, cacao and sesame. The amount of the substances is not specifically restricted as long as the saccharide derivatives of α,α-trehalose are capable of enhancing the effect of the above substances having moisturizing effect alone or in combination with other ingredients. It is usually 0.1-40%, preferably 0.5-20% to total amount of the external dermatological formulation.

Particularly, the saccharide derivatives of α,α-trehalose of the present invention more strongly improve the moisturizing effect and skin feeling in combination with hyaluronic acid or mucopolysaccharides, more particularly hyaluronic acid, among the above substances. Hyaluronic acid used in the present invention is restricted to special molecular weight as long as it is enhanced in its moisturizing effect by saccharide derivatives of α,α-trehalose. The molecular weight of hyaluronic acid is usually 600,000-2,500,000, preferably 800,000-2,200,000.

The term "substances having whitening effect" includes L-ascorbic acid derivatives and/or alkali metal or alkaline earth metal salts thereof such as L-ascorbic acid, L-ascorbic acid glycosides including L-ascorbic acid 2-glucoside, acyl derivatives of L-ascorbic acid 2-glycoside, ascorbyl tetrahexyldeconate, ascorbic acid tocopherol phosphate diesther, L-ascorbic acid sulfate esther, ascorbyl dipalmitate, ascorbyl palmitate, stearyl L-ascorbate, L-ascorbyl phosphate, ethyl L-ascorbate, acyl derivatives thereof; lactic acid, kojic acid, ellagic acid or derivatives thereof and/or alkali metal salts or alkaline earth metal salts, tranexamic acid, phytic acid, glutathione, hydroquinone or derivatives thereof including arbutin, plants or ingredients thereof having whitening effect such as chamomilla ET, "RUCINOL®" (4-n-Butylresorcinol), chamomile extract, brown sugar extract, arbutin (a kind of glycosyl hydroquinone), glycyrrhiza, mori cortex, uva-ursi, bilberry extract, houttuynia herb extract, deer horn shape ganoderma lucidum extract, iris, clove, turmeric, capsicum, karela, aloe, tea leaf, glycyrrhiza, scutellaria root, chamomile, mori cortex, pueraria root, *Xanthoxylum piperitum*, moutan bark, gingko, rose fruit, *Coptis rhizome, Hypericum erectum*, gardenia, *Sophorae radix*, rice, rice bran, asiasarum root, peony root, cnidium root, mori cortex, tea leaf, Japanese angelica root, *Calendula officinalis*, hamamelis, safflower, *Amethyst sage*, gambir, hackberry, *Diospyros kaki*, sage, Japanese radish, azalea, parsley, hop and coix seed; animal ingredients such as placenta extract; and inorganic substance such as sulfur. The amount of the substances is not specifically restricted as long as the saccharide derivatives of α,α-trehalose are capable of enhancing the effect of the above substances having whitening effect alone or in combination with other ingredient. It is usually 0.001-5%, preferably 0.01-3% to total amount of the external dermatological formulation. In the case of less than 0.001%, they are expected to exert the desired effect. In the case of more than 5%, they are not dose-dependently effective.

The term "substances having antioxidant effect" as referred to as in the present invention includes plants or plants ingredients having antioxidant effect such as vitamin A or derivatives thereof, vitamin B or derivatives thereof, L-ascorbic acid or derivatives thereof, vitamin D or derivatives thereof, vitamin E or derivatives thereof, dibutyl hydroxy toluene, butyl hydroxy anisole, superoxide dismutase, mannitol, carotenoids, astaxanthin, rutin or derivatives thereof, rutin, hesperidin, quercetin, catechin, epicatechin, epigallocatechin, or derivatives thereof including saccharide derivatives, gallic acid or derivatives thereof, glutathione or derivatives thereof, glutathione, β-carotenes or derivatives thereof, ubiquinol, flavonoids, polyphenols, sweet hydrangea leaf, turmeric, rose fruit, echinacea, *Scutellaria root, Hypericum erectum*, Chinese gall nut, *Geranium thunbergii*, rice, rice bran, comfrey, *Xanthoxylum piperitum*, labiate, peony root, soybean, "Natto" (soybeans fermented in their own bacteria), tea leaf, clove, loquat, peony, horse chestnut, saxifrage, rooibos, rosemary, spirulina, chlorella and dunaliella. In addition, they include bilirubin, cholesterol, tryptophan, histidine, thiotaurine and hypotaurine. The amount of the substances is not specifically restricted as long as the saccharide derivatives of α,α-trehalose are capable of enhancing the effect of the above substances having antioxidant effect alone or in combination with other ingredient. It is usually 0.0001-5%, preferably 0.001-2% to total amount of the external dermatological formulation. In the case of less than 0.0001%, they are expected to exert the desired effect. In the case of more than 5%, they are not dose-dependently effective. The saccharide derivatives of α,α-trehalose inhibit the browning of L-ascorbic acid. Therefore, more amount of L-ascorbic acid or derivatives thereof can be used for external dermatological formulation in combination the saccharide derivatives of α,α-trehalose.

The term "substances having UV-absorbing effect" as referred to as in the present invention include benzoate compounds such as paraaminobenzoic acid (PABA), PABA monoglycerin esther, N,N-dipropoxy PABA ethyl esther, N,N-diethoxy PABA ethyl esther, N,N-dimethyl PABA ethyl esther, N,N-dimethyl PABA butyl esther; anthranilate compounds such as homomenthyl-N-acetyl anthranilate; salicylate compounds such as amyl salicylate, menthyl salicylate, homomenthyl salicylate, octyl salicylate, phenyl salicylate, benzyl salicylate, p-isopropanol phenyl salicylate; cinnamate compounds such as octyl cinnamate, ethyl-4-isopropylcinnamate, methy-2,5-diidopropylcinnamate, ethy-2,4-diisopropylcinnamate, methy-2,4-diisopropylcinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethy-p-methoxycinnamate, cyclohexyl-p-methoxy cinnamate, ethyl-α-cyano-β-phenyl cinnamate, 2-ethylhexyl-α-cyano-β-phenyl cinnamate and glyceryl mono-2-ethylhexanoyl-diparamethoxycinnnmate; benzophenone compound such as 2,4-dihydroxy benzophenone, 2,2'-dihydroxy-4-methoxy benzophenone, 2,2'-dihydroxy-4,4'-dimethoxy benzophenone, 2,2',4,4'-tetrahydroxy benzophenone, 2-hydroxy-4-methoxy benzophenone, 2-hydroxy-4-methoxy-4'-methyl benzophenone, 2-hydroxy-4-methoxy benzophenone-5-sulfonate, 4-phenyl benzophenone, 2-ethylhexyl-4'-phenyl-benzophenone-2-carboxylate and 2-hydroxy-4-n-octoxy benzophenone; 3-(4'-methylbenzylidene)-d,l-camphor, 3-benzylidene-d,l-camphor, urocanic acid, urocanic acid ethyl esther, 2-phenyl-5-methybenzoxazol, 2,2'-hydroxy-5-methylphenylbenzotriazole, 2-(2'-hydroxy-5'-t-octylphenyl) benzotriazole, 2-(2'-hydroxy-5'-methylphenyl)benzotriazole, dibenzalazine, dianisoyl methane, 4-methoxy-4'-t-butyldibenzoylmethane, rutin, hesperidine, quercetin, or derivatives thereof including saccharide derivatives. The amount of the substances is not specifically restricted as long as the saccharide derivatives of α,α-trehalose are capable of enhancing the effect of the above substances having UV-absorbing effect alone or in combination with other ingredient. It is usually 0.0001-40%, preferably 0.01-20% to total amount of the external dermatological formulation. In the case of less than 0.0001%, they are expected to exert the desired effect. In the case of more than 40%, they are not dose-dependently effective.

The term "substances having UV-scattering effect "as referred to as in the present invention include titanium oxide, zinc oxide, selenium oxide, zirconium oxide; iron oxide, or clay minerals such as kaolin, talc, mica and sericite. The amount of the substances is not specifically restricted as long as the saccharide derivatives of α,α-trehalose are capable of enhancing the effect of the above substances having UV-scattering effect alone or in combination with other ingredients. It is usually 0.0001-40%, preferably 0.01-20% to total amount of the external dermatological formulation. In the case of less than 0.0001%, they are expected to exert the desired effect. In the case of more than 40%, they are not dose-dependently effective.

The term "substances having emulsifying effect" as referred to as in the present invention includes any one or more non-ionic surfactants and/or ionic surfactants. Example of non-ionic surfactants are sorbitan fatty acid esthers such as sorbitan monolaurate and sorbitan sesquiisostearate; glycerin fatty acid esthers such as glycerin monooleate and glycerin monoisostearate; polyglycerin fatty acid esthers such as diglyceryl monooleate and decaglyceryl diisostearate; polyoxyethylene sorbitan fatty acid esthers such as polyoxyethylene sorbitan monooleate (6 E.O.) and polyoxyethylene sorbitan monooleate (20 E.O.); polyoxyethylene sorbit fatty acid esthers such as polyoxyethylene sorbit monolaurate (6 E.O.) and polyoxyethylene sorbit tetraoleate (40 E.O.); polyoxyethylene glycerin fatty acid esthers such as polyoxyethylene glyceryl monooleate (5 E.O.) and polyoxyethylene glyceryl monooleate (15 E.O.); polyethylene glycol fatty acid esthers such as polyoxyethylene monoisostearate (10 E.O.) and polyoxyethylene monooleate; polyoxyethylene glycol difatty acid esthers such as polyoxyethylene diisostearate (8 E.O.) and polyoxyethylene diisostearate; polyoxyethylene alkyl ether such as polyoxyethylene oleyl ether (7 E.O.) and polyoxyethylene oleyl ether (10 E.O.); polyoxyethylene polyoxypropylene alkyl ether such as polyoxyethylene(1) polyoxypropylene(4) alkyl ether; and polyoxyethylene caster oil/wax such as polyoxyethylene caster oil (20 E.O.) and polyoxyethylene caster wax (40 E.O.). In addition, they include propylene glycol fatty acid esthers or ethylene oxide derivatives, polyether denaturation silicone, trehalose mono-fatty acid esthers, trehalose difatty acid esthers, trehalose derivatives such as saccharide derivatives of trehalose fatty acid esthers, sucrose fatty acid esthers, and saccharide derivatives such as alkyl glucoside.

The ionic surfactant is divided into anionic, cationic and amphoionic surfactant. Example of the anionic surfactants are higher fatty acids, alkyl sulfate esthers such as alkyl benzene sulfate and α-olefin sulfate, polyoxyethylene alkyl ether sulfate, acyl N-methyl taurinate, alkyl ether phosphate esther, N-acyl amino acid, alkyl amide phosphate, alkyl ether carbonate, or alkali metal, alkaline earth metal, alkanolamin ion, ammonium ion or basic amino acid salts thereof. Example of cationic surfactants are alkyl trimethyl ammonium chloride, dialkyl dimethyl ammonium chloride, benzalkonium chloride, and alkyl benzyl methyl ammonium. Example of amphoionic surfactants are betaine type amphoionic surfactants such as betaine alkyl dimethyl aminoacetate, betaine alkyl amide propyl dimethyl amino acetate and 2-alkyl-N-carboxymethyl-N-hydroxyethyl imidazolium betaine; amino acid type amphoionic surfactants such as imidazoline type amphoionic surfactants, triethanolamine N-cocoacyl-L-glutamate and potassium N-cocoacyl-L-glutamate; and non-ionic surfactants such as polyoxyethylene type surfactants, polyalcohol esther type surfactants and ethylene oxide/propylene oxide block polymers. The substances having emulsifying effect also include high polymer type surfactants and substances having emulsifying effect such as polyvinyl alcohol, sodium alginate, starch derivatives, cyclodextrins, anhydrous crystalline maltose, tragacanth gum, lecithin, saponin, isoflavones and phosphatidylcholine.

Varying the purpose of the external dermatological formulation in the present invention, total HLB value of the formulation is preferably 6-13. Particularly, when used as cleansing cosmetics, the formulation is hard to be washed out under HLB 6 and is lowered in oil-solubility over HLB 13. Polyoxyethylene diisostearate (10 E.O.) or polyoxyethylene isostearate (10 E.O.) is preferably used in the present invention. Alkyl groups in the above substances having emulsifying effect have usually 8-26 carbon atoms, preferably 8-22, more preferably 12-18.

The amount of the substances is not specifically restricted as long as the saccharide derivatives of α,α-trehalose are capable of enhancing the effect of the above substances alone or in combination with other ingredients. It is usually 0.0001-50%, preferably 0.01-40% to total amount of the external dermatological formulation. The substances are preferably contained in the formulation as cleansing cosmetics in an amount of 6.0-35%. The formulation is hard to solubilize oily ingredients in the solution containing saccharide derivatives of α,α-trehalose under 6.0%.

The term “substances having astringent effect” as referred to as in the present invention includes any substance as long as it has astringent effect. Example of the substances are menthol, camphor, alum, chlorohydroxy aluminum, ammonium chloride, allantoin aluminum salt, zinc sulfate, metal salts of ammonium sulfate such as aluminum potassium sulfate, zinc sulfophenate, naringin, naringin derivatives such as glycosyl naringin, organic acid such as tannic acid, citric acid, lactic acid and succinic acid. Further, examples of the substances are plants or plants ingredients including gambir, Sweet hydrangea leaf, *Althea officinalis* root, aloe, fennel, rose fruit, St. John’s wort, *Lamium album*, orange, sea weed, valerian, *Artemisa capillaris*, bramble, kiwi, gentian, *Geranium thunbergii*, Chinese gall nut, maybush, meadowsweet, white birch, crataegi fructus tree, bourtree, juniper, nosebleed, sage, thyme, tea leaf, *Potantilla tormentilla*, nettle, coltsfoot, grape, hop, horse chestnut, balm mint, cornflower, wormwood, apple, lemon, *Astragalus sinicus*, rosehip, Lonicera japonica, peony root, horse tail, clematis and ivy. The amount of the substances is not specifically restricted as long as the saccharide derivatives of α,α-trehalose are capable of enhancing the effect of the above substances having astringent effect alone or in combination with other ingredients. It is usually 0.0003-10%, preferably 0.001-5% to total amount of the external dermatological formulation.

The term “substances having wrinkle-reducing effect” as referred to as in the present invention includes any substance as long as it has wrinkle-reducing effect. Examples of the substances are retinoids such as retinol, retinoic acid and retinal, pangamic acid, kinetin, ursolic acid, turmeric extract, sphingosine derivatives, silicon, silica, N-methyl-L-serine and mevalonolactone. The amount of the substances is not specifically restricted as long as the saccharide derivatives of α,α-trehalose are capable of enhancing the effect of the above substances having wrinkle-reducing effect alone or in combination with other ingredients. It is usually 0.0003-10%, preferably 0.01-5% to total amount of the external dermatological formulation.

The term “substances having cell-activating effect” as referred to as in the present invention includes any substance as long as it has cell-activating effect. Example of the substances are amino acids such as γ-aminobutyric acid and ϵ-aminocaporonic acid, vitamins such as retinol, thiamine, riboflavin, pyridoxine chloride and pantothenic acids, α-hydroxy acids such as glycolic acids and lactic acid, tannin, flavonoids, saponin, allantoin Kanko-so No. 301 and plant components of “gagome” oarweed, rockweed, *Undaria pinnatifida*, Lessoniaceae, *Nemacystus decipiens* or *Pterocladia capillacea*. The amount of the substances not specifically restricted as long as the saccharide derivatives of α,α-trehalose are capable of enhancing the effect of the above substances having cell-activating effect alone or in combination with other ingredients. It is usually 0.0003-10%, preferably 0.001-5% to total amount of the external dermatological formulation.

The term “substances having transdermal absorption-promoting effect” as referred to as in the present invention includes any substance as long as it has transdermal absorption-promoting effect. Example of the substances are urea, lactic acid, fruit acids, α-hydroxy acids such as glycolic acid, sulfur, β-hydroxy acids such as salicylic acid, oleic acid, undecanoinic acid, octanol, nonanol, menthol, thymol, limonene, dimethylsulfoxide (DMSO), dodecyl methyl sulfoxide, dimethyl lacetamide, N,N-dimethyl formamide, sodium rauryl sulfate, N,N-bis(2hydroxy ethyl)oleylamine, polyoxyethlene (20) sorbitan monooleate, dodecyl dimethyl ammoniopropanesulfate, propylene glycol, polyethylene glycol, n,n-dimethyl-m-toluamide, DEET (diethyl-m-toluamide), laurocapram, cyclodextrin, 1-dodecylazacycloheptane-2-on, isopropyl myristate, isopropyl palmitate, N-(mono or di)-p-mentane-3-carboxyamide, 2-(2-methoxy-1-methylethyl)-5-methylcyclohexanol or azacycloalkane derivatives. The above substances can be used in combination. The amount of the substances is not specifically restricted as long as the saccharide derivatives of α,α-trehalose are capable of enhancing the effect of the above substances having cell-activating effect alone or in combination with other ingredients. It is usually 0.0003-20%, preferably 0.001-10%, more preferably 0.01-5% to total amount of the external dermatological formulation. The external dermatological formulation of the present invention can be optionally promoted to penetrate into skins by a delivery system for effective ingredients using liposomes and/or by iontophoresis devices disclosed by the present applicant in Japan Patent Publication Nos. 345,977/02 and 105,515/04. These methods can be used in combination with one or more the above substances having transdermal absorption-promoting effect.

The formulation of the present invention optionally comprises other ingredients for usual external dermatological formulation. Example of the ingredients are powders, oils, fats, edetic acid, di-, tri- or tetrasodium edetate, sodium citrate, oxycarbonic acids or alkaline metal salts thereof such as lactic acid and sodium lactate, chelating agents such as ethylenediamine tetra acetate or alkaline metal salts or alkaline earth metal salts thereof and sodium metaphosphate, antioxidants such as butylhydroxy toluene (BHT), butylhydroxy anisol (BHA) and propyl gallate, water, alcohols such as ethanol and isopropanol, oily substances such as liquid paraffin, vaseline, microcrystalline wax, squalane, ceramide, sweet almond oil, olive oil, hardened oil, caster oil, Japan wax, coconut oil, bees was, lanolin, carnauba wax and palm oil, sterols such as phytosterol, fatty acids such as lanolic acid, myristic acid, palmitic acid, stearic acid, isostearic acid and oleic acid, or triglyceride thereof, higher alcohols such as rauryl alcohol, cetanol, stearyl alcohol, oleyl alcohol and cholesterol, esthers such as isopropyl myristate, myristyl myristate and isopropyl palmitate, other inorganic or organic acids including α-hydroxy acids or acetic acid such as phosphoric acid, citric acid, malic acid, tartaric acid, lactic acid and succinic acid, or salts thereof, inorganic or organic alkaline agent such as sodium hydrate, potassium hydrate and triethanolamine, or salts thereof, fullerene or derivatives thereof, colorants such as yellow iron oxide, titan yellow and carthamin, vitamins such as thiamine, nicotinamide, riboflavin, L-ascorbic acid, pyrrolo-quinoline quinone, carotenoide, ergosterol and tocopherol, naringin, glycosyl naringin, photosensitizing dyes such as Kanko-so No. 101 (platonin), Kanko-so No. 301 (takanal), Kanko-so No. 401 and plarumin, tar colorants such as Red No. 104, Yellow No. 4, Yellow No. 5, Green No. 3, Blue No. 1, Blue No. 2, Red No. 202, Red No. 226, Red No. 227, Red No. 230, Orange No. 206, Orange No. 207, Yellow No. 202, Green No. 201, Green No. 204, Blue No. 201 and Green No. 205, synthetic lake colorants from carminic acid, laccaic acid, carthamin, brazilin and crocin, natural colorants such as anthraquinone, anthocyanin and carotenoid dyes including carthamus colour, gardenia colour, lithospermum root colour, cochineal colour, turmeric colour, monascus colour, beet colour, lac colour, madder colour, perilla colour, red cabbage colour, red radish colour, elderberry colour, blueberry colour, paprika colour, annatto colour, spirulina colour, cacao colour, tamarind colour, Japanese persimmon colour, kaoliang colour and caramel colour, ingredients used in bath salts such as sulfur, sodium bicarbonate, sodium chloride, mint, mineral spring, sodium carbonate, sinter, borax, *Cnidium rhizome*, Japanese angelica root and *Schizonepetae herba*.

The term "powder" as referred to as in the present invention is not specifically restricted. Examples of the powder are inorganic powder such as talc, kaolin, sericite, white mica, synthetic mica, red mica, black mica, lithia mica, vermiculite, magnesium carbonate, calcium carbonate, diatomite, magnesium silicate, calcium silicate, aluminum silicate, barium silicate, strontium silicate, metal salts of tungstate, α-iron oxide, iron oxide hydrate, silica and hydroxyapatite; organic powder such as nylon powder, polyethylene powder, benzoguanamine powder, ethylene tetrafluoride powder, distylenebenzen pinhole polymer powder, polysaccharide powders including microcrystalline cellulose, celluloid powder, acetylcellulose powder, cellulose powder, starch powder, chitin powder and chitosan powder, and protein powders including silk powder and scleroprotein powder, inorganic white pigments such as titanium oxide and zinc oxide; inorganic red pigments such as iron oxide(colcothar) and iron titanate; inorganic yellow pigments such as yellow iron oxide and yellow ocher; inorganic violet pigments such as mango violet and cobalt violet; inorganic green pigments such as chromium oxide, chromium hydride and cobalt titanate; inorganic blue pigments such as ultramarine blue and Prussian blue; pearl pigments such as titanium oxide-coated mica, titamiun oxide-coated bismuth oxychloride, bismuth oxychloride, titanium oxide-coated talc, fish scale guanine, colored titanium oxide-coated mica; and metal powder pigments such as aluminum powder and copper powder. In addition, powdered hydrophobes thereof or the above inorganic powders or organic powders bound with the above synthetic colorants and/or natural colorants can be used. The amount of the substances is not specifically restricted as long as the saccharide derivatives of α,α-trehalose are capable of enhancing the effect of the above substances. It is usually 0.0003-95%, preferably 0.01-80%, more preferably 0.01-75% to total amount of the external dermatological formulation.

The word "oil and fat" as referred to as in the present invention is not specifically restricted. Examples of the oil and fat are synthetic oils or fats such as medium chain triglyceride; plant oils or fats such as soybean oil, rice oil, rape oil, cotton oil, sesame oil, safflower oil, caster oil, olive oil, cacao oil, camellia oil, sunflower seed oil, palm oil, linseed oil, perilla oil, shea oil, sal oil, coconut oil, Japan wax, jojoba oil, grape seed oil and avocado oil; animal oils or fats such as mink oil, egg yolk oil, beef tallow, milk fat and lard; waxes such as bees wax, spermaceti, lanolin, carnauba wax and candelila wax; hydrocarbons such as liquid paraffin, squalene, squalane, microcrystalline wax, ceresin wax, paraffin wax and vaseline; natural and synthetic fatty acid such as lauric acid, myristic acid, stearic acid, oleic acid, isostearic acid and behenic acid; natural and synthetic higher alcohols such as cetanol, stearyl alcohol, hexyl decanol, octyl decanol and rauryl alcohol; esthers or ethers such as isopropyl myristate, isopropyl palmitate, octyldodecyl myristate and cholesterol oleate; and silicone oil.

When containing gums such as carboxyvinylpolymer or acrylate/metaacrylate co-polymer and substances having inhibitory effect on the gel-formation such as ascorbic acid 2-glucoside, the external dermatological formulation of the present invention can be produced in a manner of adding polyethylene glycol and dipropylene glycol together with the gums and adjusting to pH 5.5-7.5, preferably pH 5.9-7.0, to be a gel form having a high viscosity, satisfactory out looking, and transparency. The above gel has satisfactory skin feeling without occurring kink or dirt characteristic to cosmetics containing water-insoluble high polymer such as 1,3-butylene glycol and 1,2-pentanediol. The amounts of polyethylene glycol and dipropylene glycol are not specifically restricted as long as the formulation is formed into a gel having a high viscosity, satisfactory transparency and skin feeling. The amount of polyethylene glycol is usually 0.05-20%, preferably 0.5-5% to total amount of the formulation. The amount of dibutylene glycol is usually 0.05-20%, preferably 0.5-5% to total amount of the formulation.

The amount of gums such as carboxyvinylpolymer and polyacrylate polymer are not specifically restricted as long as the formulation is formed into a gel having a high viscosity, satisfactory transparency and skin feeling. It is usually 0.05-15%, preferably 0.5-10%, more preferably 0.5-2% to total amount of the formulation.

The external dermatological formulation of the present invention can contain the substances having water-solubilizing effect for the purpose of stabilizing aqueous substances such as ascorbic acid. Examples of such substances having water-solubilizing effect are lower alcohols, higher alcohols such as glycerin, ethylene glycol and propylene glycol, hydrogenated soybean phospholipids, polyoxyethylene sorbitan fatty acid esthers, polyoxyethylene lanolin alcohols, polyoxyethylene caster oil, polyoxyethylene caster wax, polyoxyethylene sterol, polyoxyethylene alkyl ethers, polyoxyethylene, polyoxypropylene alkyl ethers or polyoxyethylene alkyl phenyl ethers. Preferable examples are ethanol, glycerin, ethylene glycol, propylene glycol, 1,3-butylene glycol, diethylene glycol, dipropylene glycol, hydrogenated soybean phospholipids, polyoxyethylene sorbitan fatty acid esthers, polyoxyethylene lanolin alcohols, polyoxyethylene caster oil, polyoxyethylene caster wax or polyoxyethylene alkyl ethers.

When produced with carbomer type of acrylic polymer or gums mixture containing isoparaffin, polyacrylamide and polyoxyethylene rauryl alcohol as main ingredients, as gums or stabilizers, the formulation of the present invention preferably contains 1-8% on a dry solid basis of saccharide derivatives of $\alpha,\alpha$-trehalose to a final weight in the manner of adding the saccharide derivatives or a saccharide mixture containing the same to the gums mixture until swelling with water. As result, the formulation is easily emulsified due to the improvement of water-solubility of the gums mixture, and efficiently produced. In order to improve skin feeling, 1,3-butylene glycol is optionally added to the formulation in an amount of 0.5-3.0% to the final product together with saccharide derivatives of $\alpha,\alpha$-trehalose.

The external dermatological formulation can comprise one or more members selected from the group consisting of lymphokines such as interferon-$\alpha$, interferon-$\beta$, interferon-$\gamma$, tumor necrosis factor-$\alpha$, tumor necrosis factor-$\beta$, macrophage migration inhibitory factor, colony stimulating factor, transfer factor, interleukin-2; hormones such as insulin growth hormone, prolactin, erythropoietin, follicle stimulating hormone and steroids; antibiotics such as penicillin, erythromycin, chloramphenicol, tetracycline, streptomycin and kanamycin sulfate; enzymes such as lipase, elastase, urokinase, protease, $\beta$-amylase, isoamylase, glucanase and lactase; ginseng; aloe; mallow; iris; grape seed; coix seed; balm mint; nosebleed; loofah; lily; phellodendron bark; peony root; sialid; birch; loquat; chlorella; propolis extract; fungus such as redcurrants, *Ganoderma lucidum*, deer horn shape *Ganoderma lucidum* and *Phellinus linteus*; plant extract such as herbs; animal extracts such as snapping turtle extract; seaweed extract such as *Enteromorpha compressa* extract and yellow green layer extract; royal jelly; galenicals; high intensity sweeteners such as dihydrochalcone, stevioside, $\alpha$-glycosyl stevioside, rebaudioside, glycyrrhizin, L-aspartyl-L-phenylalanine methyl esther, acesulfame-K and sucralose, saccharin; minerals or compounds thereof such as calcium, magnesium, iron, manganese, cobalt, copper, zinc, phosphorus, selenium, fluorine and iodine; alkaline ionized water; acidic ionized water; and magnetized water.

If necessary, the external dermatological formulation can also comprise one or more substances used for pharmaceuticals, quasi-drugs, cosmetics or toiletries, described in "Japanese Standard of Cosmetic Ingredients", "Supplement to the Japanese of Cosmetic Ingredients codex", "Japanese Cosmetic Ingredients Codex by Category", "Japanese Quasi-drug Ingredients Codex", "The Japanese Pharmacopoeia", Supplement to the Japanese Pharmacopoeia codex", Japanese Standards of Pharmaceutical Additive", "Japanese Standards of Herbal Medicine", "The Japanese Standards of Food Additives", "Latest Cosmetic Science (Saishin Keshohin Kagaku), revised and enlarged edition II", published by The Yakuji Nippo Ltd, in Jul. 10, 1992, "New Cosmetology (Shin Keshohingaku)", published by Nanzando Co. Ltd., in Jan. 18, 2002, or "Cosmetic and Toiletry Formulation, 2nd edition", Vol. 8, published by William Andrew Publisher, in 2001. Examples of such ingredients are pharmaceuticals, excipients, bases, emollients, cooling agents, astringents, refrigeratives, surfactants, emulsifiers, dispersing agents, solubilizing agents, solvents, alkaline chemicals, thickening agents, gums, film-forming agents, foaming agents, antifoaming agents, perfumeries, coloring agents, stabilizers, antiseptics, bactericides, discoloration inhibitory agents, antioxidants, hair treating agents, humectants, hair-protecting agents, tricks activator agents, antielectrostatic agents, solvents, solubilizing agents, plasticizers, suspending agents, buffering agents, sweeteners, refrigeratives, sweetening agents, binders, absorbents, propellants, coating agents, masticatories, fillers, softeners, adjusters, chelating agents, discoloration inhibitory agents, oils, fats, oil-soluble polymer, inorganic or organic pigments, inorganic or organic pigments treated with silicone or fluoro compounds, pigments such as organic dyes, photosensitizing dyes such as rumin, waxes, antiperspirants, deodorants, anti-wrinkle agents, sebum secretion inhibitors, antiseborrheic agents, parakeratosis inhibitors, horny layer removers, horny layer resolving agents, analgestics, torpents, antiplasmic agents, nutritional supplements, antiandrogenic agents, antihistamic agents, phosphodiesterase inhibitors, adipose cell differentiation inhibitory agents, lipase inhibitors, collagenase inhibitors, tyrosinase inhibitors, fibroblast activating agents, and collagen-production promoting agents. If necessary, food ingredients can be used. The above ingredients can be used in any amount for the external dermatological formulation of the present invention as long as they do not affect the desired effects.

Any form of the formulation can be used; for example, solution form, emulsion form, powder-dispersion form, water-oil form, water-powder form or water-oil-powder form. The formulation of the present invention can be used as base cosmetics, finishing cosmetics, skin cosmetics, cleansing cosmetics, face washes, skin lotions, creams, milky lotions, packs, foundations, face powders, powders, rouges, eyebrow, eye and cheek care cosmetics, perfume, bath cosmetics, oral care cosmetics, tanning cosmetics, sun care cosmetics, makeup cosmetics, nail cosmetics, eye liner cosmetics, mouth and lip care cosmetics, oral care cosmetics, facial care cosmetics, cosmetic oils, fragrant cosmetics, body care cosmetics, hair care cosmetics, hair wash cosmetics, cosmetic soaps, medicated soaps, toothpaste, oral refrigeratives, hircismus blockers, bath dusting powders, hair growth promoters, tonics, shaving cosmetics, sunscreens, antiiching agents, wiping and cleaning agents, bactericide, disinfectant, decolorants and depilatories, further, preventing or treating agent for athlete's foot, hemorrhoids, acnes, wounds, burns, chilblains, rashes, festers, inflammations, infections, allergies, atopic diseases, ulcers or tumors in the form of a skin lotion, lotion, milky lotion, cream, ointment, plaster, suspension, emulsion, paste, mousse, tic, solid, semisolid, powder, solid powder, mid-container forming powder, block, pencil, stick, jelly, gel, aerosol, spray, lozenge, pack or facemask. Example of such cosmetics are cosmetic soaps, face cleansing creams, cleansing foams, cleansing milks, cleansing lotions, cleansing oils, massage creams, cold creams, moisture creams, vanishing creams, hand creams, moisture lotions, cosmetic oils, liquid foundations, powder foundations, cake foundations, stick foundations, oily compact foundations, creamy foundations, cheek blushers, emulsified foundations, foundation cosmetics, body powders, creamy face powders, face powders, liquid face powders, solid face powders, talcum powders, wet face powders, loose shadows, baby powders, cheek colors, pencils, mascaras, lipsticks, lip creams, packs, shaving creams, after shaving creams, lotions, hand lotions, shaving lotions, after shaving lotions, sun screen creams, tanning oils, sun screen lotions, tanning lotions, softening skin lotions, astringent skin lotions, cleansing skin lotions, multi-layer skin lotions, facial shampoos, body shampoos, hair shampoos, hair-washing powders, hand soaps, facial rinses, body rinses, hair rinses, hair treatments, pilatories, tonics, tics, pomades, hair creams, hair liquids, hair tonics, set lotions, combing oils, combing oils for side hair, hair sprays, hair mousses, hair tonics, hair dyes, hair bleachers, color rinses, color sprays, permanent wave liquids, press powders, loose powders, eye creams, eye shadows, cream eye shadows, powder eye shadows, eye liners, eye blow pencils, mascaras, depilatory creams, perfumes, kneaded perfumes, powder perfumes, eau de cologne, deodorants, bath preparations, bath oils, bath salts, cosmetic oils, baby oils, nail colors, enamels, enamel removers, nail treatments, mouth washes, toothpastes, tooth powders, insect repellers, ointments for treating wounds, antibacterial creams, steroid ointments, and further, cataplasms in the form of sheet or film, laundry soaps or detergents for clothes, detergents for flower, detergents for kitchen and cleansers.

The saccharide derivatives of α,α-trehalose used in the present invention are stable even in the strong acidic or alkaline condition. Therefore, the external dermatological formulation of the present invention can be adjusted to any pH suitable for use thereof. The pH is usually 3-12. When the formulation is a cream or skin lotion, it is preferably adjusted to pH4-12, and more preferable pH5-9 nearer to skin's pH. When the formulation is a cleansing us such as soaps or shampoos, it is usually adjusted to a neutral and alkaline side, and possibly to round pH 13. When the formulation is a soap, the saccharide derivatives of α,α-trehalose prevent the formulation to be cloudy and yellowish, and enable to produce a transparent soap. The formulation of the present invention can be adjusted to any osmotic pressure. If it is a skin lotion having a higher water-content, it is preferably adjusted to osmotic pressure of 200-600 mOsm in order to be lowered in the stimulation to skins.

The following experiments explain the external dermatological formulation according to the present invention in detail.

Experiment 1

Influence of Saccharide Derivatives of α,α-trehalose on Substances having Antiinflammatory Effect To confirm the influence of saccharide derivatives of α,α-trehalose and/or glycyrrhizinic acid on the burned skins due to the inflammation after sunbath, the following experiment was carried out. Skin lotions containing glycyrrhizinic acid, which is used generally as a cosmetic ingredient having an effect on inhibiting the inflammation of skins due to sunburn, and α-glucosyl α,α-trehalose or α-maltosyl α,α-trehalose, which is a kind of saccharide derivatives of α,α-trehalose, were prepared for the following experiment to confirm the influence on the burn of skins after sun bath. As shown in Table 1, skin lotion (formulation No. 1) was prepared by admixing a base preparation consisting of 3.0 parts by weight of ethanol, 10.0 parts by weight of 1,3-butylene glycol, 0.5 part by weight of polyoxyethylene(15) oleylalcohol ether, 0.1 part by weight of oleylalcohol, 0.1 part by weight of ethyl paraben and 0.02 part by weight of perfumery with an appropriate amount of purified water to give a final weight of 100 parts by weight. Skin lotions (formulation Nos. 2-4) were prepared by adding either of 0.5 part by weight on a dry solid basis of hydrous crystalline α-glucosyl α,α-trehalose (purity 99.0% or more) prepared according to Experiment B-1 of Japanese Patent Publication (Kokai) No. 291,986/95, 0.5 part by weight on a dry solid basis of a powdery α-maltosyl α,α-trehalose (purity 98.1%) prepared according to the following Example 5, or 0.5 part by weight of glycyrrhizinic acid to the base preparation and admixed with an appropriate amount of purified water to give a final weight of 100 parts by weight. Skin lotions (formulation Nos. 8-10) were prepared by adding 0.5, 1.5 or 5.0 parts by weight, on a dry solid basis of the powdery α-maltosyl α,α-trehalose (purity 98.1%) and 0.5 part by weight of glycyrrhizinic acid to the base preparation, and admixing with an appropriate amount of purified water to give a final weight of 100 parts by weight.

Method of Test

Thirteen panels (women aged 20s and 30s) were asked to use the skin lotions (formulation Nos. 1-10) for two days in a prescribed manner after enjoying a sea bathing in a summer beach for a half day. Then, they were asked the questionnaires; satisfaction with the antiinflammatory effect (effect on suppressing the burn of the skins in their backs, shoulders and outside of upper parts of their arms), and the skin feeling in terms of sticky feeling and refreshness. Table 1 shows the numbers of panels who were satisfied with the effect for each skin lotion, and the percentages thereof (%). Table 1 also shows the numbers of panels satisfied with the skin feeling without sticky feeling in the skins for each skin lotion and the percentages thereof (%)

TABLE 1

| | Ingredient | Amount (part by weight) No. 1 | No. 2 | No. 3 | No. 4 | No. 5 | No. 6 | No. 7 | No. 8 | No. 9 | No. 10 |
|---|---|---|---|---|---|---|---|---|---|---|---|
| Glycyrrhizinic acid | | 0.0 | 0.0 | 0.0 | 0.5 | 0.5 | 0.5 | 0.5 | 0.5 | 0.5 | 0.5 |
| α-Glucosyl α,α-trehalose (dry solid basis) | | 0.0 | 0.5 | 0.0 | 0.0 | 0.5 | 1.5 | 5.0 | 0.0 | 0.0 | 0.0 |
| α-Maltosyl α,α-trehalose (dry solid basis) | | 0.0 | 0.0 | 0.5 | 0.0 | 0.0 | 0.0 | 0.0 | 0.5 | 1.5 | 5.0 |
| Base ingredient | Ethanol | 3.0 | 3.0 | 3.0 | 3.0 | 3.0 | 3.0 | 3.0 | 3.0 | 3.0 | 3.0 |
| | 1,3-Butyleneglycol | 10.0 | 10.0 | 10.0 | 10.0 | 10.0 | 10.0 | 10.0 | 10.0 | 10.0 | 10.0 |
| | Polyoxyethylene(15) oleylalcoholether | 0.5 | 0.5 | 0.5 | 0.5 | 0.5 | 0.5 | 0.5 | 0.5 | 0.5 | 0.5 |
| | Oleylalcohol | 0.1 | 0.1 | 0.1 | 0.1 | 0.1 | 0.1 | 0.1 | 0.1 | 0.1 | 0.1 |
| | Ethylparaven | 0.1 | 0.1 | 0.1 | 0.1 | 0.1 | 0.1 | 0.1 | 0.1 | 0.1 | 0.1 |
| | Perfumeries | 0.0 | 0.0 | 0.0 | 0.0 | 0.0 | 0.0 | 0.0 | 0.0 | 0.0 | 0.0 |
| | Purified water | remainder | remainder | remainder | remainder | remainder | remainder | remainder | remainder | remainder | remainder |
| Total | | 100.0 | 100.0 | 100.0 | 100.0 | 100.0 | 100.0 | 100.0 | 100.0 | 100.0 | 100.0 |
| Judgement | Panels satisfied with the effect on suppressing burn | 0 (0) | 1 (8) | 1 (8) | 4 (31) | 8 (62) | 13 (100) | 13 (100) | 9 (69) | 13 (100) | 13 (100) |
| | Panels satisfied with the effect on skin feeling | 5 (38) | 13 (100) | 13 (100) | 4 (31) | 8 (62) | 11 (85) | 13 (100) | 9 (69) | 13 (100) | 13 (100) |

As evident from the result in Table 1, the skin lotions; formulation No. 2 containing 0.5 part by weight of α-glucosyl α,α-trehalose (concentration of 0.5%), and formulation No. 3 containing 0.5 part by weight of α-maltosyl α,α-trehalose (concentration of 0.5%), were judged to have satisfactory effect on suppressing the burn by only 8% of panels. The skin lotion; formulation No. 4 containing 0.5 part by weight of glycyrrhizinic acid (concentration of 0.5%) was judged to have satisfactory effect on suppressing the burn by about 31% of panels. Among the skin lotions containing 0.5 part by weight of glycyrrhizinic acid, formulation No. 5 containing 0.5 part by weight of α-glucosyl α,α-trehalose (concentration of 0.5%, on a dry solid basis), and formulation No. 8 containing 0.5 part by weight of α-maltosyl α,α-trehalose (concentration of 0.5%, on a dry solid basis), were judged to have satisfactory effect on suppressing the burn by 62% and 69% of panels, respectively. Further, among the skin lotions containing 0.5 part by weight of glycyrrhizinic acid (concentration of 5%, on a dry solid basis), the skin lotions containing 1.5 parts by weight of α-glucosyl α,α-trehalose (concentration of 1.5%, on a dry solid basis: formulation No. 6), 5.0 parts by weight of α-glucosyl α,α-trehalose (concentration of 5.0%, on a dry solid basis: formulation No. 7), 1.5 parts by weight of α-maltosyl α,α-trehalose (concentration of 1.5%, on a dry solid basis: formulation No. 9), and 5.0 parts by weight of α-maltosyl α,α-trehalose (concentration of 5.0%, on a dry solid basis: formulation No. 10) were judged to have satisfactory effect on suppressing the by all panels. These results reveal that α-glucosyl α,α-trehalose or α-maltosyl α,α-trehalose, which is a kind of saccharide derivatives of α,α-trehalose, is capable of enhancing the antiinflammatory effect of glycyrrhizinic acid in a dose dependent manner.

As regards the skin feeling, skin lotion containing only base ingredients without α-glucosyl α,α-trehalose or α-maltosyl α,α-trehalose (formulation No. 1), was judged to have satisfactory skin feeling by 38% of panels. In contrast, skin lotions containing 0.5 part by weight of α-glucosyl α,α-trehalose (concentration of 0.5%, on a dry solid basis: formulation No. 2), and containing 0.5 part by weight of α-maltosyl α,α-trehalose (concentration of 0.5%, on a dry solid basis: formulation No. 3) were judged to have satisfactory skin feeling by all panels. Further, skin lotion, containing 0.5 part by weight of glycyrrhizinic acid (concentration of 0.5%, on a dry solid basis: formulation No. 4) to 100 parts by weight of the skin lotion together with only base ingredients, was judged to have satisfactory skin feeling by 31% of panels. In contrast, the skin lotions, further containing 0.5 part by weight of α-glucosyl α,α-trehalose (concentration of 5%, on a dry solid basis: formulation No. 5) and 0.5 part by weight of α-maltosyl α,α-trehalose (concentration of 5%, on a dry solid basis: formulation No. 8), were judged to have satisfactory skin feeling by 62% and 69% of panels, respectively. Furthermore, skin lotions, containing 1.5 parts by weight of α-glucosyl α,α-trehalose (concentration of 1.5%, on a dry solid basis: formulation No. 6), 1.5 parts by weight of α-maltosyl α,α-trehalose (concentration of 1.5%, on a dry solid basis: formulation No. 9), on a dry solid basis, together with 0.5% of glycyrrhizinic acid to 100 parts by weight of the skin lotion (concentration of 0.5%, on a dry solid basis) and base ingredients, were judged to have satisfactory skin feeling by 85% and 100% of panels, respectively. In addition, the skin lotions, further containing 5 parts by weight of α-glucosyl α,α-trehalose (concentration of 5.0%, on a dry solid basis: formulation No. 7) and α-maltosyl α,α-trehalose (formulation No. 10) were judged to have satisfactory effect by all panels. These results reveal that α-glucosyl α,α-trehalose or α-maltosyl α,α-trehalose has the effects on suppressing sticky feeling of the skin lotion containing only base ingredients or containing base ingredients and glycyrrhizinic acid to improve skin feeling.

Experiment 2

Influence of Saccharide Derivatives of α,α-trehalose on Substances Having Blood Flow-promoting Effect Fallen hair and itch of the head skins are sometimes caused by an insufficient blood flow. To confirm the influence of saccharide derivatives of α,α-trehalose and/or substances having blood flow-promoting effect on the blood flow of head skins, the following experiment was carried out.

Preparation of Saccharide Derivatives of α,α-trehalose

The syrup containing saccharide derivatives of α,α-trehalose, prepared in Example 1, was hydrogenated according to Example 6 to convert reducing saccharides in the syrup into corresponding sugar alcohols. After separated from Raney nickel, the resulting solution was decolored, desalted, and concentrated to obtain a syrup. The syrup, containing 0.8% of α-glucosyl α,α-trehalose, 52.8% of α-maltosyl α,α-trehalose, 1.3% of α-maltotriosyl α,α-trehalose, 7.7% of other saccharide derivatives of α,α-trehalose, 1.9% of sorbitol, 8.0% of maltitol, 10.7% of maltotriitol, 16.6% of maltotetraitol, and 0.2% of other sugar alcohols, had a concentration of 75%.

Preparation of Hair Tonics as Test Samples

As shown in Table 2, 4.6 parts by weight of the above syrup containing saccharide derivatives of α,α-trehalose (2.0 parts by weight of saccharide derivatives of α,α-trehalose, on a dry solid basis), were admixed with two or three substances having blood flow-promoting effect selected from 1.0 part by weight of sialid extract, 1.0 part by weight of ginseng extract and 0.5 part by weight of α-dl-tocopherol, and further admixed with 60.0 parts by weight of ethylalcohol, 2.0 parts by weight of propylene glycol, and up to 100 parts by weight of water to prepare hair tonics (Formulation Nos. 1-4). 4.6 parts by weight of the same syrup prepared in Example 1 was admixed with any one of one part by weight of sialid extract, 1.0 part by weight of ginseng extract and 1.0 part by weight of α-dl-tocopherol, and further admixed with 60.0 parts by weight of ethylalcohol, 2.0 parts by weight of propylene glycol, and up to 100 parts by weight of water to prepare hair tonics (formulation Nos. 5-8).

Method of Test

Eleven panels (males aged 40s and 50s), having itch of their head skins due to insufficient blood flow, were asked to use the hair tonics (formulation Nos. 1-8) for 14 days in a manner of spreading an appropriate amount of each hair tonic over their head skins two times a day. Then, they were asked the questionnaires; suppressing effect against fallen hair or itch of head skins. The hair tonics were compared with each other in view of the skin feeling including sticky feeling and refreshing feeling after use. Table 2 shows the numbers of panels were satisfied with the suppressing effect of each hair tonic on fallen hair and itch of head skin, and the percentages thereof (%). Table 2 also shows the numbers of panels satisfied the skin feeling without sticky feeling against skins of each skin lotion and the percentages thereof (%).

TABLE 2

| Ingredient | | Amount (part by weight) | | | | | | | |
|---|---|---|---|---|---|---|---|---|---|
| | | No. 1 | No. 2 | No. 3 | No. 4 | No. 5 | No. 6 | No. 7 | No. 8 |
| Saccharide derivatives of α,α-trehalose (Dry solid basis) | | 2.0 | 2.0 | 2.0 | 2.0 | 2.0 | 0.0 | 0.0 | 0.0 |
| Ethanol | | 60.0 | 60.0 | 60.0 | 60.0 | 60.0 | 60.0 | 60.0 | 60.0 |
| Sialid extract | | 1.0 | 1.0 | 0.0 | 1.0 | 0.0 | 1.0 | 0.0 | 0.0 |
| Ginseng extract | | 0.0 | 1.0 | 1.0 | 1.0 | 0.0 | 0.0 | 1.0 | 0.0 |
| α-dl-Tocopherol | | 0.5 | 0.0 | 0.5 | 0.5 | 0.0 | 0.0 | 0.0 | 0.5 |
| Propylene glycol | | 2.0 | 2.0 | 2.0 | 2.0 | 2.0 | 2.0 | 2.0 | 2.0 |
| Purified water | | Remainder | Remainder | Remainder | Remainder | Remainder | Remainder | Remainder | Remainder |
| Total | | 100.0 | 100.0 | 100.0 | 100.0 | 100.0 | 100.0 | 100.0 | 100.0 |
| Judgement | Panels satisfied with the effect on suppressing fallen hair (%) | 10 (91) | 10 (91) | 10 (91) | 10 (91) | 1 (9) | 3 (27) | 3 (27) | 4 (36) |
| | Panels satisfied with the effect on suppressing itch (%) | 8 (73) | 9 (82) | 8 (73) | 10 (91) | 2 (18) | 3 (27) | 4 (36) | 3 (27) |
| | Panels satisfied with the effect on skin feeling (%) | 11 (100) | 11 (100) | 11 (100) | 11 (100) | 11 (100) | 5 (45) | 6 (55) | 4 (36) |

As evidence from the result in Table 2, hair tonic containing only 2.0 parts on a dry solid basis by weight of saccharide derivatives of α,α-trehalose to 100 parts be weight of hair tonic together with ethanol and propylene glycol, (concentration of 2.0%: Formulation No. 5) was not judged to have a satisfactory effect on suppressing itch of head skins or fallen hair. Hair tonic containing only 1.0 part by weight of sialid extract (concentration of 1.0%: Formulation No. 6), 1.0 part by weight of ginseng extract (concentration of 1.0%: formulation No. 7), or 0.5 part by weight of α-dl-tocopherol (concentration of 1.0%: formulation No. 8) to 100 parts by weight of hair tonic together with ethanol and propylene glycol were judged to have a satisfactory effect on suppressing fallen hair by 27%, 27% and 36% of panels, respectively, and itch of head skins by 27%, 36% and 27% of panels, respectively. In contrast, hair tonics containing two parts by weight of saccharide derivatives of α,α-trehalose (concentration of 2.0%) and two or three of 1.0 part by weight of sialid extract (concentration of 1.0%), 1.0 part by weight of ginseng extract (concentration of 1.0%) and 0.5 part by weight of α-dl-tocopherol (concentration of 0.5%) together with ethanol and propylene glycol were judged to have a satisfactory effect on fallen hair by 91% of panels. As regards the effect on suppressing the itch of head skin, hair tonic containing two parts on a dry solid basis by weight of saccharide derivatives of α,α-trehalose (concentration of 2.0%), 1.0 part by weight of sialid extract (concentration of 1.0%), 0.5 part by weight of α-dl-tocopherol (concentration of 0.5%) together with ethanol and propylene glycol to 100 parts by weight of hair tonic (formulation No. 1) was judged to have a satisfactory effect by 73% of panels; hair tonic containing two parts on a dry solid basis by weight of saccharide derivatives of α,α-trehalose (concentration of 2.0%), 1.0 part by weight of sialid extract (concentration of 1.0%), 1.0 part by weight of ginseng extract (concentration of 1.0%: formulation No. 2) was judged to have a satisfactory effect by 82% of panels; hair tonic containing 2 parts on a dry solid basis by weight of saccharide derivatives of α,α-trehalose (concentration of 2.0%), 1.0 part by weight of ginseng extract (concentration of 1.0%), 0.5 part by weight of α-dl-tocopherol (concentration of 0.5%: formulation No. 3) was judged to have a satisfactory effect by 73% of panels; hair tonic containing 2 parts on a dry solid basis by weight of saccharide derivatives of α,α-trehalose (concentration of 2.0%), 1.0 part by weight of sialid extract (concentration of 1.0%), 1.0 part by weight of ginseng extract (concentration of 1.0%), 0.5 part by weight of α-dl-tocopherol (concentration of 0.5%: formulation No. 4) was judged to have a satisfactory effect by 91% of panels. These results reveal that saccharide derivatives of α,α-trehalose are effective on suppressing fallen hair and itch of head skins in combination with two or three of substances having blood flow-promoting effect such as sialid extract, ginseng extract and α-dl-tocopherol.

As regards to skin feeling, hair tonics without saccharide derivatives of α,α-trehalose (formulation Nos. 6-8) were judged to have satisfactory effect on skin feeling by 36-55% of panels. In contrast, hair tonics containing 2.0 parts by weight of saccharide derivatives of α,α-trehalose (concentration of 2.0%: Formulation Nos. 1-5) were judged to have a satisfactory effect on skin feeling by all of 11 panels with or without substances having blood flow-promoting effect. These results reveal that saccharide derivatives of α,α-trehalose are effective on suppressing sticky feeling and improving skin feeling of hair tonic containing ethanol, propylene glycol and purified water and hair tonic containing ethanol, propylene glycol, purified water and substances having blood flow-promoting effect.

Experiment 3

Influence of Coexisting with Saccharide Derivatives of α,α-trehalose on Easily Browning Substances Used for Usual External Dermatological Formulation Various substances, used for external dermatological formulation, sometime cause of browning (including coloring) in the case of combination use with other substances. To confirm the influence of combination of L-ascorbic acid, used as a substance having antiinflammatory effect for external dermatological formulation and known to cause of browning, and saccharide derivatives of α,α-trehalose, the following experiment was carried out.

Preparation of Test Solution 13.3 parts by weight of the syrup containing saccharide derivatives of α,α-trehalose (10.0 parts by weight of solid base of saccharides), used in Experiment 2, and 1.0 part by weight of L-ascorbic acid were dissolved in an appropriate amount of purified water. The resulting solution was adjusted to about pH 6.5, and admixed with purified water to prepare 100 parts by weight of an aqueous solution. As a control, an aqueous solution was prepared by dissolving 1.0 part by weight of L-ascorbic acid in an appropriate amount of purified water, adjusting to about pH 6.5 and admixing with water to give a final weight of 100 parts. An aqueous solution further containing 10 parts by weight of glycerin (concentrated glycerin in cosmetic grade, commercialized by Kao Co., Ltd., Tokyo, Japan) instead of saccharide derivatives of α,α-trehalose was prepared.

Method of Test

Three resulting solutions were kept at 50° C. under the shaded condition for 14 days. To examine browning, values of absorbance 420 nm of the test samples were measured by usual method and compared with that of the starting test samples. To examine the degree of coloring, relative values of test samples were calculated by comparing the value of differential absorbance of the solution containing only L-ascorbic acid, defined as 100%.

TABLE 3

| Ingredient | Absorbance of starting test sample (420 nm) | Absorbance of test sample kept after 14 days (420 nm) | Difference of absorbance (420 nm) | Degree of coloring (%) |
|---|---|---|---|---|
| L-Ascorbic acid | 0.001 | 5.000 | 4.999 | 100 |
| L-Ascorbic acid + Glycerin | 0.001 | 3.064 | 3.063 | 61 |
| L-Ascorbic acid + Saccharide derivatives of α,α-trehalose | 0.001 | 1.353 | 1.352 | 27 |

Degree of coloring=(Difference of absorbance of test sample containing saccharide derivatives of α,α-trehalose or glycerin)/(Difference of absorbance of control sample containing only L-ascorbic acid)×100

As evidence from the result in Table 3, the aqueous solution containing L-ascorbic acid was observed to be a strong browning after two weeks. The aqueous solution containing L-ascorbic acid and saccharide derivatives of α,α-trehalose was lowered to about 27% of the degree of solution containing no saccharide derivatives of α,α-trehalose. The aqueous solution containing L-ascorbic acid and glycerin was lowered to about 61% of the degree of solution containing no glycerin. Saccharide derivatives of α,α-trehalose more strongly inhibited the browning of L-ascorbic acid than glycerin did. These results reveal that saccharide derivatives of α,α-trehalose are effective on inhibiting the browning of L-ascorbic acid. A syrup at the concentration of 75%, containing about 53% of α-maltosyl α,α-trehalose and 5% of other saccharide derivatives of α,α-trehalose, on a dry solid basis, as a material of the syrup before hydrogenation used in this experiment, was examined in view of influence to browning of L-ascorbic acid according to Experiment 3. As a result, it is revealed to have almost equal effect to the hydrogenated saccharide mixture containing saccharide derivatives of α,α-trehalose, used in Experiment 3, in view of inhibition of the browning of L-ascorbic acid. The same experiment to the above except to co-existing of 10 mM iron ion was carried out. As a result, saccharide mixture containing saccharide derivatives of α,α-trehalose inhibited the browning of L-ascorbic acid. Therefore, it is suggested to have chelating activity against iron ion.

Experiment 4

Influence of Saccharide Derivatives of α,α-trehalose on Moisturizing Skins

To confirm the influence of saccharide derivatives of α,α-trehalose on moisturizing skins, the following experiment using hyaluronic acid as a positive control was carried out.

Preparation of Test Skin Lotion

As shown in Table 4, one part by weight of 1,2-pentandiol, one part by weight of 1,3-butylene glycol, two parts by weight of ethanol, one part by weight of "Hyaluronic Acid FCH", a 1% aqueous hyaluronic acid solution (molecular weight 1,800,000-2,200,000) commercialized by Kibun Food Chemifa Co., Ltd., Tokyo, Japan, and/or 5.2 parts by weight on a dry solid basis of syrup containing saccharide derivatives of α,α-trehalose (3.0 parts by weight on a dry solid basis of saccharide derivatives of α,α-trehalose), used in Experiment 2, were dissolved in an appropriate amount of purified water. The resulting solution was admixed with purified water to give a final weight of 100 parts by weight to prepare test skin lotions (formulation Nos. 1-3).

Method of Test

Influence of test skin lotions on the moisture of the skins was judged by measuring conductance as a reference for hydration level of skin. At first, the conductance of skin surface at the body side of upper right arm of all panels consisting of 15 males and 15 females were measured using "SKICON-200EX", a skin surface hygrometer commercialized by I.B.S Co., Ltd., Shizuoka, Japan, before using the test skin lotions. Then, panels were randomly divided into three groups consisting of five males and five females. Panels were applied with one of the skin lotions formulation Nos. 1-3 listed in Table 4, at the same positions (skin surface at the body side of upper right arm) pre-measured above. After air drying for five minutes, the conductance at the positions was measured using the skin surface hygrometer. Table 4 shows the averages of 10 panels of each group.

TABLE 4

| | | Formulation | | |
|---|---|---|---|---|
| | | No. 1 | No. 2 | No. 3 |
| 1,2-Pentanediol | | 1.0 | 1.0 | 1.0 |
| 1,3-Butylene glycol | | 1.0 | 1.0 | 1.0 |
| Ethanol | | 2.0 | 2.0 | 2.0 |
| Hyaluronic acid (1% aqueous solution) | | 1.0 | 0.0 | 1.0 |
| Syrup containing saccharide derivatives of α,α-trehalose (Dry solid basis) | | 0.0 | 5.2 | 5.2 |
| Purified water | | Appropriate amount | Appropriate amount | Appropriate amount |
| Total amount | | 100 | 100 | 100 |
| Moisture content (μS) (Relative value) | Before | 43 | 41 | 40 |
| | After | 52 (121) | 75 (183) | 84 (210) |

As evidence from the result in Table 4, the average of conductance having a relation with moisture content of skin surface before applying the skin lotion was about 40-43 micro Siemens (μS), and the average of conductance after applying the skin lotion containing 0.01% of hyaluronic acid to total weight was 52 μS meaning 21% increase as compared with that of before applying. In contrast, the average of conductance after applying the skin lotion containing 5.2% on a dry solid basis of the syrup containing saccharide derivatives of α,α-trehalose was 83% increase as compared with that of before applying. Further, the average after applying the skin lotion containing 0.01% of hyaluronic acid and 5.2% of the syrup containing saccharide derivatives of α,α-trehalose was 84 μS meaning 110% increase as compared with that of before applying. These results reveal that saccharide derivatives of α,α-trehalose imparts the moisturizing effect to skins and has a satisfactory effect as a moisturizing agent for external dermatological formulations, and the moisturizing effect of the saccharide derivatives of α,α-trehalose is further enhanced in combination with hyaluronic acid. In addition, as regards skin feeling after applying the test skin lotion, all panels judged that the skin lotion containing saccharide derivatives of α,α-trehalose had less sticky feeling and more satisfactory skin feeling than that of only hyaluronic acid. All panels also judged that the skin lotion containing both of hyaluronic acid and the syrup containing saccharide derivatives of α,α-trehalose had more satisfactory skin feeling than that of single use thereof.

The following examples explain the present invention. The following examples explain saccharide material containing saccharide derivatives of α,α-trehalose and process thereof, and its use for external dermatological formulations. The present invention is not restricted to only these examples.

Example 1

A corn starch was prepared into an about 20% of starch suspension, admixed with calcium carbonate to give a final concentration of 0.1%, and adjusted to pH 6.5. The resulting solution was admixed with 0.2%/g-starch on a dry solid basis of "TERMAMYL 60L", an α-amylase commercialized by NovoZyme A/S, Bagsværd, Denmark, and followed by the enzyme reaction at 95° C. for 15 minutes. After autoclaved at 120° C. for 10 minutes, the resulting reaction mixture was cooled to 50° C., adjusted to pH 5.8, admixed with 5 units/g-starch of maltotetraose-forming amylase disclosed in Japanese Patent Publication (Kokai) No. 240,784/88, commercialized by Hayashibara Biochemical Laboratories Inc., Okayama, Japan, and 500 units/g-starch of isoamylase commercialized by Hayashibara Biochemical Laboratories Inc., Okayama, Japan, and followed by the enzymatic reaction for 48 hours. The reaction mixture was further admixed with 30 units/g-starch of "α-AMYLASE 2A", α-amylase commercialized by Ueda Chemical Industries Co., Ltd., Hyogo, Japan and followed by the enzyme reaction at 65° C. for four hours. After autoclaved at 120° C. for 10 minutes, the reaction mixture was cooled to 45° C., admixed with 2 units/g-starch of a non-reducing saccharide-forming enzyme originated from *Arthrobacter* sp. Q36 (FREM BP-4316), disclosed in Japanese Patent Publication (Kokai) No. 143,876/95, and followed by an enzymatic reaction for 48 hours. The reaction mixture was kept at 95° C. for 10 minute, cooled and filtered to obtain a filtrate. According to conventional manner, the resulting filtrate was decolored with activated charcoal, desalted and purified with ion exchangers in H- and OH-forms, and concentrated into 70% syrup in a yield of about 90% to the material starch on a dry solid basis. The syrup showed DE 13.7 and contained 52.5% of α-maltosyl α,α-trehalose (alias α-maltotriosyl α-glucoside), 4.1% of α-glucosyl α,α-trehalose (alias α-maltosyl α-glucoside), 1.1% of α-maltotriosyl α,α-trehalose (alias α-maltotetraosyl α-glucoside), and 0.4% of other α-glycosyl α,α-trehalose, on a dry solid basis, as saccharide-derivatives of α,α-trehalose. The syrup enhances the effects of substances having any one of blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect. It also has a satisfactory moisturizing effect without sticky feeling. Therefore, it can be advantageously used as a material for external dermatological formulation.

Example 2

The syrup prepared in Example 1 was spray-dried in a usual manner to prepare an amorphous powder. The product shows a low hygroscopicity and a satisfactory solubility in water, and is advantageously used as a material for external dermatological formulation as well as Example 1.

Example 3

A saccharified solution, desalted with ion exchangers in H-form and OH-form, prepared in Example 1, was subjected to a column chromatography using "DOWEX 50W-X4 ($Mg^{2+}$-form)", a strong acid cation-exchange resin commercialized by Dow Chemical Company, Michigan, USA. The resin was packed into four jacketed stainless steel columns having an inner diameter of 5.4 cm, which were then cascaded in series to give a total gel bed depth of 20 m. Under the conditions of keeping the inner column temperature at 55° C., the saccharide solution was fed to the columns in a volume of 5% (v/v) and fractionated by feeding to the columns hot water heated to 55° C. at an SV (space velocity) of 0.13 to remove high content fractions of glucose and maltose, and then high content fractions of saccharide-derivative of α,α-trehalose were collected. The resulting saccharide solution was further purified and concentrated, and then spray-dried to prepare an amorphous powder comprising saccharide-derivatives of α,α-trehalose in a high content. The product contained 70.2% of α-maltosyl α,α-trehalose, 6.1% of α-glucosyl α,α-trehalose, 2.1% of α-maltotriosyl α,α-trehalose, and 4.1% of other α-glycosyl α,α-trehalose, on a dry solid basis, as saccharide-derivatives of α,α-trehalose. Since the product shows a low hygroscopicity and a satisfactory solubility in water, it is advantageously used as a material for external dermatological formulation as well as Example 1.

Example 4

One part by weight of a potato starch dissolved in six parts by weight of water was admixed with "NEOSPITASE", an α-amylase commercialized by Nagase & Co., Ltd., Osaka, Japan, to give a final concentration of 0.01%/starch, and adjusted to pH 6.0. The resulting starch suspension was kept at 85 to 90° C. to be gelatinized and liquefied simultaneously until DE 1.0 and heated immediately at 120° C. for five minutes. Then, the solution was rapidly cooled to 55° C., adjusted to pH 7.0, admixed with 150 units/g-starch on a dry solid basis of "PULULLANASE", an pullulanase (EC 3.2.1.41) commercialized by Hayashibara Biochemical Laboratories Inc., Okayama, Japan, and eight units/g-starch on a dry solid basis of maltotetraose-forming amylase, disclosed in Japanese Patent Publication (Kokai) No. 240,784/88, commercialized by Hayashibara Biochemical Laboratories Inc., Okayama, Japan, and followed by the enzymatic reaction at 50° C. and pH 7.0 for 36 hours. After autoclaved at 120° C. for 10 minutes, the reaction mixture was cooled to 53° C., admixed with 2 units/g-starch of non-reducing saccharide-forming enzyme originated from *Arthrobacter* sp. S34 (FREM BP-6450), disclosed in Japanese Patent Publication (Kokai) No. 228,980/00, and followed the enzymatic reaction for 64 hours. The reaction mixture was kept at 95° C. for 10 minutes, cooled and filtered to obtain a filtrate. According to the conventional manner, the resulting filtrate was decolored with activated charcoal, desalted and purified with ion exchangers in H- and OH-forms, and then concentrated. The concentrate was spray-dried to obtain an amorphous powder containing saccharide-derivatives of α,α-trehalose in a yield of about 90% to the material starch on a dry solid basis. The product showed DE 11.4 and contained 62.5% of α-maltosyl α,α-trehalose, 2.1% of α-glucosyl α,α-trehalose, 0.8% of α-maltotriosyl α,α-trehalose, and 0.5% of other α-glycosyl α,α-trehalose, on a dry solid basis. Since the product shows a low hygroscopicity and a satisfactory solubility in water, it is useful as a material for external dermatological formulation as well as Example 1.

Example 5

Aqueous solution containing 20% of a reagent grade maltotetraose (purity 97.0% or higher), commercialized by Hayashibara Biochemical Laboratories Inc., Okayama, Japan, was admixed with two units/g-saccharide of non-reducing saccharide-forming enzyme, disclosed in Japanese Patent Publication (Kokai) No. 143,876/95, and followed by the enzymatic reaction at 46° C. for 48 hours to obtain a saccharide solution containing 79.8% of α-maltosyl α,α-trehalose on a dry solid basis. After adjusted to pH 6.0, the saccharide solution was admixed with 10 units/g-saccharide of β-amylase, commercialized by Nagase & Co., Ltd., Osaka, Japan, and followed by the enzymatic reaction at 50° C. for 48 hours for the purpose of hydrolyzing maltotetraose. After autoclaved at 120° C. for 10 minutes, the reaction mixture was cooled and filtrated. The resulting filtrate was subjected to a column chromatography using "XT-1016 (Na+-form, degree of cross linking 4%)", a strong acid cation-exchanger resin commercialized by Rohm and Hass Japan K.K., Fukushima, Japan, to collect fractions highly containing α-maltosyl α,α-trehalose. The saccharide solution was purified, concentrated, and spray-dried to obtain an amorphous powder highly containing α-maltosyl α,α-trehalose. The product, containing 98.1% of α-maltosyl α,α-trehalose, has a low reducing power less than the detection limit of Somogyi-Nelson method. Since the product shows a low hygroscopicity and a satisfactory solubility in water, it is useful as a material for external dermatological formulation. Since the product shows no reducibility, it is advantageously used as a material for external dermatological formulation comprising compounds inactivated by Maillard reaction such as amino acid and compounds having amino groups.

Example 6

The syrup containing saccharide derivatives of α,α-trehalose, prepared in Example 1, was dissolved in water to give a saccharide concentration of about 60% and admixed with about 8.5% of Raney nickel. The mixture was autoclaved at 128° C. with stirring and treated with hydrogen at a pressure of 80 $kg/cm^2$ to convert reducing sugars coexisting with saccharide-derivatives of α,α-trehalose, such as glucose and maltose, into corresponding sugar alcohols. After separated from Raney nickel, the resulting solution was decolored, desalted, and concentrated to obtain syrup at the concentration of 75%. The product is a non-color and transparent solution contains about 2.0% of α-glucosyl α,α-trehalose, about 54.3% of α-maltosyl α,α-trehalose, about 1.6% of α-maltotriosyl α,α-trehalose, about 5.2% of other saccharide derivatives of α,α-trehalose, about 4.4% of sorbitol, about 5.4% of maltitol, about 9.4% of maltotriitol, about 16.3% of maltotetraitol, and about 1.4% of other sugar alcohols. The product enhances the effects of substances having any one of blood flow-promoting effect, antiinflammatory effect, antibacterial effect, moisturizing effect, whitening effect, UV-absorbing effect, UV-scattering effect, antioxidant effect, hair growing effect, hair nourishing effect, astringent effect, wrinkle-reducing effect, cell-activating effect and transdermal absorption-promoting effect. The product is stable against the change of temperature or humidity. It keeps its low hygroscopicity even in a high humidity condition. Since the product gives skins a smooth feeling and refresh feeling without sticky feeling and has a satisfactory moisture retaining activity when applied, is suitable as materials for external dermatological formulations. Since the product has no reducibility, it is particularly suitable as a material for external dermatological formulations containing ingredient affect with browning or denaturation due to Mailard reaction such as amino acids and compounds having amino groups as well as in Example 1.

Viscosity at 20° C., 30° C., 40° C., 50° C., or 60° C. of this syrup or diluted solutions thereof (at a concentration of 10%, 20%, 30%, 40%, 50%, 60% and 70%, on a dry solid basis), prepared by diluting the syrup in an appropriate amount of purified water, was measured by "B type Viscometer" commercialized by Tokyo Keiki Co. Ltd., Tokyo, Japan. Table 5 shows the result. The 10% solution was heated at 120° C. for 30, 60 or 90 minutes. The heated samples and the unheated sample (the solution before heating) were measured with absorbance 480 nm to determine the degree of coloring. And, the content of α-maltosyl α,α-trehalose of each sample was measured. Table 6 shows the result. The content of α-maltosyl α,α-trehalose of each sample was represented by relative value to that of the unheated sample defined as 100%.

TABLE 5

| Concentration | Viscosity (mPa · s) | | | | |
|---|---|---|---|---|---|
| (Dry solid basis, %) | 20° C. | 30° C. | 40° C. | 50° C. | 60° C. |
| 10 | 1 | 1 | 1 | 1 | 1 |
| 20 | 3 | 2 | 2 | 1 | 1 |
| 30 | 4 | 3 | 3 | 2 | 2 |
| 40 | 9 | 6 | 5 | 4 | 3 |
| 50 | 26 | 17 | 11 | 8 | 7 |
| 60 | 139 | 77 | 46 | 31 | 22 |
| 70 | 1772 | 755 | 369 | 200 | 121 |
| 75 | 8844 | 3345 | 1418 | 666 | 351 |

TABLE 6

| Heating time (minute) | Degree of coloring | Content of α-maltosyl α,α-trehalose |
|---|---|---|
| Unheated | 0.009 | 100 |
| 30 | 0.007 | 100 |
| 60 | 0.008 | 100 |
| 90 | 0.011 | 100 |

As evidence from the result in Table 6, saccharide derivatives of α,α-trehalose and co-existing hydrogenated saccharides from reducing saccharides such as glucose and maltose were not colorized by heating at 120° C. for 90 minutes. In addition, α-maltosyl α,α-trehalose as s main ingredient was hardly decomposed. Therefore, the syrup was revealed to be satisfactorily heat-stable.

Property on Absorbing and Releasing Moisture

Property on absorbing and releasing moisture of the syrup containing saccharide derivatives of α,α-trehalose (concentration of 75%, on a dry solid basis), prepared in Example 6, was examined by the following experiment; saturated solution of magnesium chloride hexahydrous, potassium carbonate dihydrous, magnesium nitrate hexahydrous, ammonium nitrate, sodium chloride, potassium chloride, barium chloride dihydrous, or potassium sulfate (reagent grade) was prepared by dissolving in purified water and placed in sealed chamber overnight to give a relative humidity (RH) of 33.0%, 42.7%, 52.8%, 60.0%, 75.2%, 87.2%, 90.1%, or 97.3%. Container without cap containing about 0.5 g of the product was measured and placed in the chamber without contacting the preset salt solution, and kept at 25° C. After 0.3, 1, 3, 5, 7, 10, and 14 days, the containers with the product were measured to calculate the rate of change (%) in a manner of comparing each value with the starting weight as 100%. The result is shown in Table 7.

TABLE 7

| Relative | Time course (day) | | | | | | | |
|---|---|---|---|---|---|---|---|---|
| humidity | Starting | 0.3 | 1 | 3 | 5 | 7 | 10 | 14 |
| 33.0 | 0.0 | −5.3 | −7.9 | −11.1 | −12.8 | −13.5 | −14.2 | −14.8 |
| 42.7 | 0.0 | −5.3 | −7.9 | −11.0 | −12.9 | −13.5 | −14.2 | −14.7 |
| 52.8 | 0.0 | −5.8 | −8.4 | −11.4 | −13.2 | −13.8 | −14.4 | −14.9 |
| 60.0 | 0.0 | −5.2 | −7.7 | −10.7 | −12.4 | −12.9 | −13.3 | −13.6 |
| 75.2 | 0.0 | −2.8 | −5.3 | −7.7 | −9.0 | −9.3 | −9.2 | −9.4 |
| 84.2 | 0.0 | −1.0 | −0.5 | −0.1 | −0.8 | −1.0 | −0.6 | −0.0 |
| 90.1 | 0.0 | 1.1 | 3.4 | 7.2 | 7.3 | 9.3 | 13.4 | 11.4 |
| 97.3 | 0.0 | 4.3 | 9.8 | 22.7 | 26.6 | 32.4 | 41.0 | 47.0 |

As evidence from result in Table 7, the product exerted the effect on absorbing moisture in the circumstance of RH 97.3% or 90.1%. The weight of the product increased up about 47.0% or 11.4% to the starting weight after 14 days. In the circumstance of RH 84.2%, the weight of the product did not increased. The results reveal that the product is a syrup hardly absorbing moisture in the condition of relatively high humidity. The product released moisture in the circumstance of RH 75.2% or lower. Although the weight of the product gradually decreased until 3 days, the product stably kept its moisture because the decrease of weight was not observed after 3 days. The decreasing rate depends on humidity of circumstance. The lower humidity of circumstance causes the more decreasing rate. Concretely, the weight of the product preserved in the circumstance of RH 33% for 14 days decreased about 14.8% to starting weight. In contrast, the syrup containing saccharide derivatives of α,α-trehalose, prepared in Example 1, was decreased in its weight due to releasing moisture in the circumstance of RH 84.2% that the product showed no change of weight (data not shown). The syrup prepared Example 1 was more decreased in its weight than the product in the circumstance of RH 75.2% or less. Therefore, hydrogenated syrup, containing saccharide derivatives of α,α-trehalose and sugar alcohols converted from reducing saccharides, is revealed to have better moisturizing effect than the non-hydrogenated syrup.

Test for Absorbing or Releasing Moisture

The syrup containing saccharide derivatives of α,α-trehalose was confirmed to have a satisfactory property of absorbing and releasing moisture. To compare other saccharide used as a usual moisturizing agent for cosmetics, the following experiment was carried out. Test samples, containing 75%, on a dry solid basis, of either of the syrup prepared in Example 6, concentrated glycerin, sorbitol or maltitol, were prepared. About 1 g of each solution was placed in two containers. The containers were preciously weighed and kept at RH 60% for 216 hours. One of containers was kept at RH 80% and the other container was kept at PH 33%. After 24 hours or 168 hours, they were weighed. The relative weight change rate of each test sample was calculated in such a manner of comparing each value with the weight of a control kept at RH 60% for 216 hours, which was regarded as 100%. The result is shown in Table 8.

TABLE 8

| | | Relative weight change rate (%) Time course at RH 80% or 33% (hour) | | |
|---|---|---|---|---|
| Humidity | Test sample | 0 | 24 | 168 |
| RH 80% | Glycerin | 0.0 | 8.2 | 13.1 |
| | Sorbitol | 0.0 | 5.4 | 10.7 |
| | Maltitol | 0.0 | 3.5 | 5.3 |
| | Syrup containing saccharide derivatives of α,α-trehalose | 0.0 | 1.6 | 3.0 |
| RH 33% | Glycerin | 0.0 | −13.8 | −18.8 |
| | Sorbitol | 0.0 | −2.4 | −5.0 |
| | Maltitol | 0.0 | −1.4 | −4.2 |
| | Syrup containing saccharide derivatives of α,α-trehalose | 0.0 | −0.6 | −2.3 |

As evidence from result in Table 8, test samples placed in the circumstance at RH 80% were rapidly increased in weight until 24 hours later, and gradually increased after that due to absorbing moisture. Glycerin or sorbitol showed 10% or more of the rate of increasing weight at 168 hours. In contrast, the syrup containing saccharide derivatives of α,α-trehalose showed about 3% which was the lowest of the test samples. Test samples placed in the circumstance at RH 33% were rapidly decreased in weight until 24 hours later, and gradually increased after that due to releasing moisture. Glycerin showed about 19% of the rate of decreasing weight at 168 hours. In contrast, the syrup containing saccharide derivatives of α,α-trehalose showed about 3% which was the lowest of the test samples. As evident form the above experiment and result in Experiment 4, the syrup containing saccharide derivatives of α,α-trehalose is revealed to be saccharides more hardly influenced by the humidity of the circumstance than glycerin, sorbitol or maltitol as usual cosmetic moisturizing agent in the circumstance at RH 80% or 33%. They were not sticky in higher humidity and keep moisturizing effect in lower humidity, and have a satisfactory property for a controlling agent for absorbing or releasing moisture. Therefore, the property of the saccharide derivatives of α,α-trehalose, described above, was suggested to be due to the excellent controlling effect on absorbing and releasing moisture.

Single Oral Administration Limiting Test

Five males and five females of five-weeks aged Wister rats, commercialized by Japan Charlsrever Co., Ltd., Tokyo, Japan, were forcedly administered with 2 g/kg body weight of the syrup containing saccharide derivatives of α,α-trehalose (at a concentration of 75%, on a dry solid basis), prepared in Example 6, in order to carry out single oral administration limiting test. As a control, five males and five females of five-weeks aged rats were forcedly administered with 2 g/kg body weight of purified water. Both of the groups administered with saccharide derivatives of α,α-trehalose and the control group were observed in megascopic and anatomic manners and revealed to show no disorder and death. No variation in their body weight was observed between the group administered with saccharide derivatives of α,α-trehalose and the control group. This single oral administration limiting test revealed that the limiting dose of the syrup containing saccharide derivatives of α,α-trehalose was 2 g/kg or more.

Eye Mucosa-irritation Test

Eight males and eight females of 3 to 4 months-aged New Zealand White rabbits, commercialized by Charles River Japan, Inc., Yokohama, Japan, were once administered in their right eyes with 0.2 g of the syrup containing saccharide derivatives of α,α-trehalose (at a concentration of 75%, on a dry solid basis), prepared in Example 6. As controls, they were not administrated in their left eyes with the syrup. One hour later, four male and four female rabbits were washed their eyes with physiological saline (hereinafter, called "Washed group"). The remaining four male and four female rabbits were not washed their eyes (hereinafter, called "Unwashed group"). The rabbit eyes of the washed and the unwashed groups were observed about the changes of cornea, iris and conjunctiva just after the administration of saccharide derivatives of α,α-trehalose, just after the eye washing, and one, two and three days after the eye washing. The rabbits of the washed and unwashed groups were not observed any change of cornea, iris and conjunctiva at any checking time. The result revealed that the syrup containing saccharide derivatives of α,α-trehalose gave no irritation.

Test for Cell Activation

To examine the influence of the syrup containing saccharide derivatives of α,α-trehalose, prepared in Example 6, on cell proliferation, the following experiment was carried out. The syrup was diluted with purified water and sterilized with a 0.22-μm filter to prepare a 60% solution. One volume of the resulting solution was diluted with an appropriate amount of purified water, and admixed with 10 volumes of MEM medium to prepare test media containing 6%, 0.6%, 0.06% or 0.006% on a dry solid basis of the saccharide derivatives of α,α-trehalose. Human fibroblast cells (NB1RBG), suspended with MEM medium supplemented with 1% fetal calf serum, were seeded in a 24-well microplate, and cultured in a 5% $CO_2$ incubator at 37° C. for one day. After removing medium from the wells, either of the above test media was added to the wells and changed once a day. The cells were continuously cultured for four days. As a control, the cells were cultured in the same manner and schedule except for using a control medium prepared by mixing 10 volumes of MEM medium to one volume of purified water. The cells were cultured in the wells filled with each test medium with different concentration of saccharide mixture containing saccharide derivatives of α,α-trehalose, and subjected to usual MTT assay for measuring cell amount. Each cell amount was represented by a relative value to that of the control defined as 100%. The result is shown in Table 9.

TABLE 9

| Concentration of saccharide mixture containing saccharide derivatives of α,α-trehalose (%, Dry solid basis) | Cell amount (%) |
|---|---|
| 0 | 100 |
| 0.006 | 109 |
| 0.06 | 112 |
| 0.6 | 121 |
| 6.0 | 114 |

As evidence from the result in Table 9, all the test media more increased the amount of fibroblast cell than the control medium. Particularly, the cell amount with the test medium containing 0.6% of the saccharide mixture showed 21% increase as compared with the control medium. The saccharide mixture containing saccharide derivatives of α,α-trehalose was revealed to have a cell-activating effect.

Test for Cell Protection

To examine the influence of the syrup containing saccharide derivatives of α,α-trehalose, prepared in Example 6, on cell protection, the following experiment was carried out. Mouse fibroblast cells (L-929), suspended in Dulbecco's MEM (hereinafter, called as "D-MEM") supplemented with 10% fetal calf serum, were seeded in 12 of 6-well microplates and cultured in a 5% $CO_2$ incubator at 37° C. for 2 days. The cells placed in four plates were further cultured for one day in the test medium containing D-MEM supplemented with 10% fetal calf serum and 1%, on a dry solid basis, of the syrup containing saccharide derivatives of α,α-trehalose (at the concentration of 75%, on a dry solid basis). As controls, control media containing D-MEM supplemented with 10% fetal calf serum and optionally containing 1% glycerin were prepared. The control mediums were added in the medium-removed wells of the remaining four plates, respectively. The cells were cultured for one day, dried for one hour in such a manner of keeping in opened plate under the sterile condition after the medium was removed from the wells by aspiration. Then, the cells were cultured in D-MEM supplemented with 10% fetal calf serum for three days while changing the medium once a day. The resulting plates were subjected to the measurement of cell amount of each well using "Alamar Blue" commercialized by Wako Pure Chemical Industries, Ltd., Osaka, Japan, just after the drying, and four hours, one day, two days or three days after the drying. The amounts of the cells were represented by a relative proliferation rate to that of the cells just after the one-hour-drying defined as 100%. The result is shown in Table 10. In detail, the medium was added to each well in an amount of 4 ml. One plate was used for each measurement for the amount of cells treated with the test medium or the two control mediums. The average value of the measured values from six wells was calculated by adding 40μl of "Alamar Blue" to one well and incubating four hours and measuring the cell amount by a fluorescence plate reader. The result is shown in Table 10.

TABLE 10

| Medium | Rate of cell proliferation (%) Culturing day (after dried) | | | |
|---|---|---|---|---|
| | One hour | One day | Two days | Three days |
| D-MEM containing 1% of saccharide mixture containing saccharide derivatives of α,α-trehalose (Dry solid basis) | 100 | 169 | 262 | 283 |
| D-MEM containing 1% glycerol | 100 | 165 | 235 | 243 |
| D-MEM | 100 | 163 | 234 | 238 |

As evidence from the result in Table 10, the test medium or the control media increased the rate of cell proliferation of fibroblast cells. The control medium containing 1% of glycerin increased cell amount almost equal to the control medium containing only D-MEM. In contrast, the test medium showed a higher increase rate of fibroblast cell proliferation than those with the control media. Influence caused by UV-irradiation was examined in the same manner as above instead of exposure to a drying condition (data not shown). Medium containing 1%, on a dry solid basis, of the saccharide mixture containing saccharide derivatives of α,α-trehalose showed a higher cell proliferation than the control media (D-MEM or D-MEM containing 1% of glycerin). This result reveals that a saccharide mixture containing saccharide derivatives of α,α-trehalose has a cell-protecting effect against external stresses such as drying or UV-irradiation.

Test for Prevention of the Rough Skin

To examine the influence of saccharide derivatives of α,α-trehalose on the rough skin, the following experiment was carried out. A test aqueous solution containing 10% sodium dodecyl sulfate (hereinafter, abbreviated as "SDS") and 20% of the syrup containing saccharide derivatives of α,α-trehalose was prepared. It was applied to the skin surface at the body side of the upper arm of subjects according to usual closed patch method using "Finnchamber" commercialized by Taisho Pharmaceutical Co., Ltd., Tokyo, Japan, for two hours. The treated skin surface was observed by magnifying 50 times using "Digital HD microscope VH-7000" commercialized by Keyence Corporation, Osaka, Japan. As a control, purified water was used.

When applied with an SDS solution, the skin surface was suffered from redness and inflammation. In addition, the skin folds and skin ridges became obscure and the skin texture pattern disappeared. In contrast, when applied with an SDS solution containing saccharide derivatives of α,α-trehalose, the skin surface was not suffered from inflammation. In addition, the skin folds and skin ridges were clear and the skin texture pattern finely and clearly appeared. The result reveals that a saccharide mixture containing saccharide derivatives of α,α-trehalose effectively prevents the rough skin due to surfactants such as detergents.

Test for Acidic Fermentation

To examine the effect of the syrup containing saccharide derivatives of α,α-trehalose, prepared in Example 6, on acidic fermentation, the following experiment was carried out. The syrup containing saccharide derivatives of α,α-trehalose prepared in Example 6, α-maltosyl α,α-trehalose used in Experiment 1, or sucrose was dissolved in Stephan's buffer to give a final concentration of 0.7%, on a dry solid basis, in order to prepare test saccharide solutions. *Streptocpccus mutans* OMZ-176 or *Streptococcus sobrinus* 6715, belonging to a kind cariogenetic bacteria, was cultured by the steps of slant culture, seed culture and main culture, and centrifuged to collect a bacteria precipitate. The resulting precipitate was washed with Stephan buffer (pH7.0), and centrifuged to collect a bacteria precipitate. Equal volume of Stephan buffer was added to the bacteria precipitate, followed by suspending the precipitate in the buffer to give a final concentration of 50% (v/v) in order to prepare two bacteria suspensions for testing. A half milliliter of the bacteria suspension was admixed with 0.5 ml of the above test saccharide solution and incubated at 37° C. for 90 minutes, while measuring the pH at 5, 15, 30, 60, and 90 minutes after the initiation of the culture. The result is shown in Table 11. The Stephan's buffer was prepared by admixing 1 ml of "solution A" and "solution B" with distilled water to give a final volume 100 ml, and adjusting to pH7.0 ("solution A": dissolving 71 g of $Na_2HPO_4$, 7.92 g of KOH and 68.1 g of $KH_2PO_4$ in distilled water to give a final volume 1,000 ml; and "solution B": dissolving 45.4 g of $KH_2PO_4$, 3.2 g of $MgSO_4$ $2H_2O$ and 100 ml of 1.2N HCl in distilled water to give a final volume 1,000 ml).

TABLE 11

| Bacterial strain | Test saccharide solution | pH Reaction time (minute) 0 | 5 | 15 | 30 | 60 | 90 |
|---|---|---|---|---|---|---|---|
| *S.* mutans* OMZ-176 strain | Syrup containing saccharide derivatives of α,α-trehalose, prepared in Example 6 | 6.68 | 6.61 | 6.51 | 6.49 | 6.42 | 6.41 |
| | α-Maltosyl α,α-trehalose used in Experiment 1 | 6.72 | 6.70 | 6.64 | 6.58 | 6.51 | 6.43 |
| | Sucrose | 6.60 | 4.05 | 3.97 | 3.99 | 3.99 | 4.01 |
| *S.* sobrinus* 6715 strain | Syrup containing saccharide derivatives of α,α-trehalose, prepared in Example 6 | 6.72 | 6.70 | 6.64 | 6.58 | 6.51 | 6.43 |
| | α-Maltosyl α,α-trehalose used in Experiment 1 | 6.72 | 6.70 | 6.64 | 6.58 | 6.51 | 6.43 |
| | Sucrose | 6.74 | 4.18 | 3.87 | 3.81 | 3.82 | 3.91 |

Note;
*S*: Streptococcus*

As evidence from the result in Table 11, sucrose decreased pH of the bacterial solution containing *Streptcoccus mutans* OMZ-176 or *Streptococcus sobrinus* 67115 from about 6.7 to about 4.0 for five minutes. In contrast, the syrup containing saccharide derivatives of α,α-trehalose, prepared in Example 6, and saccharide derivatives of α,α-trehalose hardly decreased pH of the bacterial solution even 90 minutes later. Therefore, these saccharides were revealed to hardly give the acidic fermentation with *Streptcoccus mutans* OMZ-176 or *Streptococcus sobrinus* 6715.

Test for the Production of Water-insoluble Glucan

To examine the effect of the syrup containing saccharide derivatives of α,α-trehalose, prepared in Example 6, on the production of water-insoluble glucan, the following experiment was carried out. According to usual method, *Streptococcus mutans* OMZ-176 was cultured to prepare a crude water-insoluble glucan producing enzyme solution (25 mg protein/ml). Test saccharide solutions were prepared by dissolving the syrup prepared in Example 1, the syrup prepared in Example 6, or α-maltosyl α,α-trehalose used in Experiment 1 in purified water to give a final concentration 2% on a dry solid basis. A half milliliter of one of the test saccharide solution was admixed with 0.25 ml of the crude water-insoluble glucan producing enzyme solution, 0.75 ml of 0.1 M phosphate buffer, and 0.5 ml of 2% sucrose. The resulting reaction mixture was placed in a new test tube (sized with 10 mm in diameter and 130 mm in height) slanted at an elevation angle of 30 degrees, and kept at 37° C. for 16 hours. The supernatant was gently collected. The remaining precipitate was washed with deionized water by centrifuging twice to collect a precipitate as adherent glucan. The washing solution and the above supernatant was mixed together and centrifuged at 5,000 rpm for 10 minutes to collect precipitate. The resulting precipitate was washed with deionized water and centrifuged to collect a non-adherent glucan. The adherent and non-adherent glucan were weighed. The total weight thereof was calculated as water-insoluble glucan. As a control, distilled water was used instead of the test saccharide solution. The water-insoluble glucan as control were weighed in the same manner. Inhibitory rate (%) of the production of water-insoluble glucan was calculated in such a manner of dividing the value of each test saccharide solution by that of the control, multiplying the resulting value by 100, and subtracting the resulting value from 100. The result is shown in Table 12.

TABLE 12

| Test saccharide solution | Production of water-insoluble glucan (μg/10 mg sucrose) (Inhibition rate of production (%)) Adhesive glucan | Non-adhesive glucan | Total glucan |
|---|---|---|---|
| Distilled water | 2222 | 1166 | 3388 |
| Syrup containing saccharide derivatives of α,α-trehalose, prepared in Example 1 | 575 (74) | 1004 (14) | 1579 (53) |
| Syrup containing saccharide derivatives of α,α-trehalose, prepared in Example 6 | 933 (58) | 1125 (4) | 2058 (39) |
| α-Maltosyl α,α-trehalose, prepared in Example 1 | 1120 (50) | 1009 (13) | 2129 (37) |

As evidence form the result in Table 12, all the test saccharide solutions inhibited the production of water-insoluble glucan from sucrose.

An additional experiment was carried out in the same manner except for without sucrose. As a result, the water-insoluble glucan was not produced from all test saccharides. These results reveal that saccharide derivatives of α,α-trehalose or saccharide mixtures containing the same are suitably used in raw materials for oral cosmetics including toothpaste to prevent dental caries.

Effect on Antiinflammation

Keratinocyte is known to produce cytokines inducing inflammation (inflammatory cytokines) such as interluekin-1β (hereinafter, it is called as "IL-1β") and TNF-α caused by external stresses illustrated with the infection of microorganisms, UV or surfactants. These inflammatory cytokines act on keratinocytes and enhance the production of inflammatory cytokine from keratinocytes. In addition, since they induce the expression of cell adhesion molecules on keratinocytes or blood vessel endothelial cells at the inflammatory skins, they make white blood cells stay there. Therefore, they cause to aggravate the inflammation at inflammatory skins.

To examine the effect of the syrup containing saccharide derivatives of α,α-trehalose, prepared in Example 6, on the inflammation, the following experiment that the production of TNF-α and expression of ICAM-1, one of the cell adhesion molecules were examined using HaCat cell, a kind of keratinocyte cell line, was carried out. Keratinocyte cell line HaCat cells were suspended in RPMI-1640 medium supplemented with 10% fetal calf serum, seeded by $5\times10^4$ cells/well in 96-well microplate and cultured overnight. After removed from the medium, the cells was admixed with RPMI-1640 supplemented with 10% fetal calf serum containing 2%, 1%, 0.5% or 0.2% (w/v) of the syrup prepared in Example 6 or concentrated glycerin (cosmetic grade) and 1 ng/ml of IL-1β, and incubated for six hours. The resulting supernatants were subjected to enzyme immunoassay using HRPO-labeled anti-human TNF-α antibody in order to measure the amount of TNF-α. To measure the amount of ICAM-1 expression, the resulting cells were fixed with 3.7% formalin, applied with anti human ICAM-1 antibody, and admixed with 4-methylumbelliferyl β-D-galactopyranoside. The resulting microplates were provided to fluorescent plate reader (excitation wavelength 355 nm, measurement wavelength 460 nm) in order to measure fluorescent intensity. As a control, cells were cultured in the only medium with the same stimulant to provide to the measurement of amount of TNF-α or ICAM-1 molecule. Inhibitory rate (%) of the production of TNF-α or ICAM-1 was calculated in a manner of dividing the value of each test medium by that of control medium and subtracting 100 times the resulting value from 100. The result of the inhibitory rate of the production of TNF-α is shown in Table 13, and that of ICAM-1 is shown in Table 14.

TABLE 13

| | Inhibitory rate of the production of TNF-α Concentration of syrup containing saccharide derivatives of α,α-trehalose or glycerin (%) | | | |
|---|---|---|---|---|
| Kind of medium | 2.0 | 1.0 | 0.5 | 0.25 |
| RPMI-1640 medium containing saccharide derivatives of α,α-trehalose | 59 | 72 | 87 | 92 |
| RPMI-1640 medium containing glycerin | 146 | 146 | 133 | 123 |

TABLE 14

| | Inhibitory rate of the production of ICAM-1 Concentration of syrup containing saccharide derivatives of α,α-trehalose or glycerin (%) | | | |
|---|---|---|---|---|
| Kind of medium | 2.0 | 1.0 | 0.5 | 0.25 |
| RPMI-1640 medium containing saccharide derivatives of α,α-trehalose | 62 | 71 | 82 | 84 |
| RPMI-1640 medium containing glycerin | 89 | 89 | 90 | 91 |

As evident from the result shown in Table 13 or 14, the syrup containing saccharide derivatives of α,α-trehalose inhibited the production of TNF-α and ICAM-1 molecule of the keratinocyte cell line HaCat cell stimulated with IL-1β in a concentration-dependent manner. Glycerin enhanced the production of TNF-α in a concentration-dependent manner and inhibited the production of ICAM-1 molecule. However, glycerin showed lower inhibitory rate than the syrup containing saccharide derivatives of α,α-trehalose did. Result of MTT method, carried out by each well after the experiment, showed almost no lowering of viability of the cell. According to the same experiment except for using macrophage cell line RAW264.7 and IFN-γ and LPS as stimulants, the syrup containing saccharide derivatives of α,α-trehalose or glycerin inhibited the production of TNF-α in a concentration-dependent manner. However, the syrup showed higher inhibitory rate than glycerin did at any concentration (data not shown).

These results suggest that saccharide derivatives of α,α-trehalose are capable of inhibiting the inflammation by applying to skin surface lowered in barrier function by the destruction of horny layers due to rough skin or inflammation, or to inflammatory head skins or mucosae. Therefore, the syrup containing saccharide derivatives of α,α-trehalose revealed to be safe and suitable as raw materials having antiinflammatory effect for external dermatological formulations.

Test for Antielectrostatic Property

To examine the effect of the syrup containing saccharide derivatives of α,α-trehalose, prepared in Example 6, on the antielectrostatic property, the following experiment was carried out. The syrup prepared in Example 6 was dropped on an acrylic plastic board and uniformly applied using a bar coater to prepare acrylic plastic board coated with a film 25 μm depth. Then, the conductance was measured by attaching the electro-rod on the surface of the acrylic plastic board. The conductor of the coated surface was $3\times10^{11}$ ohm. While, that of the uncoated surface was $1\times10^{15}$ ohm. The half life of static electricity was measured by neostmeter. The coated surface was 20 seconds or less. While, that of the uncoated surface was one minute or more. The acrylic plastic board coated with the syrup was lower than usual antielectrostatic acrylic plastic boards in the surface resistance and the half life of static electricity. That means electric charges generated by electrostatic phenomenon are quickly eliminated. The result reveals that the saccharide mixture containing saccharide derivatives of α,α-trehalose lower the static electricity on the applied surface. Therefore, the syrup is suggested to be capable of inhibiting the damages due to electrostatic phenomenon.

Example 7

The amorphous powder, containing saccharide derivatives of α,α-trehalose, prepared in Example 3, was dissolved in water to give a saccharide concentration of about 60% was admixed with about 9% of Raney nickel. The mixture was autoclaved at 130° C. with stirring and treated with hydrogen at a pressure of 75 kg/cm$^2$ to convert reducing sugars coexisting with saccharide-derivatives of α,α-trehalose, such as glucose and maltose, into corresponding sugar alcohols. After separated from Raney nickel, the resulting solution was decolored, desalted, and concentrated to obtain syrup at a concentration of 75%. Further, the syrup was spray-dried in a usual manner to obtain an amorphous powder. The product, containing about 70% of α-maltosyl α,α-trehalose and about 12% of other saccharide derivatives of α,α-trehalose on a dry solid basis, shows a low hygroscopicity and a satisfactory water-solubility and advantageously used as materials for external dermatological formulation as well as Example 1.

Example 8

About 6% starch suspension of potato starch was gelatinized by heating, adjusted to pH4.5 at 50° C., admixed with 2,500 units/g-starch of isoamylase commercialized by Hayashibara Biochemical Laboratories, Inc., Okayama, Japan and followed by the enzyme reaction for 20 hours. The resulting reaction mixture was adjusted to pH6.0 and autoclaved at 120° C. for 10 min. After cooled to 45° C., the reaction mixture was admixed with 150 units/g-starch of "TERMAMYL 60L", an α-amylase commercialized by NovoZyme A/S, Bagsværd, Denmark and followed by the enzyme reaction for 24 hours. The reaction mixture was autoclaved at 120° C. for 20 minutes. After cooled to 45° C., the reaction mixture was admixed with 2 units/g-starch of non-reducing saccharide-forming enzyme originated from *Arthrobacter* sp. Q36 (FREM BP-4316), disclosed in Japanese Patent Publication (Kokai) No. 143,876/95, and followed by the enzymatic reaction for 64 hours. The reaction mixture was kept at 95° C. for 10 minute, cooled and filtered to obtain a filtrate. According to the conventional manner, the resulting filtrate was decolored with activated charcoal, desalted and purified with ion exchangers in H- and OH-forms, and then concentrated into a 65% syrup in a yield of about 89% to the material starch on a dry solid basis. The product contains 3.2% of α-glucosyl α,α-trehalose, 6.5% of α-maltosyl α,α-trehalose, 28.5% of α-maltotriosyl α,α-trehalose, and 11.9% of α-glycosyl α,α-trehalose having six glucose residues or more. The product is used as materials for external dermatological formulation as well as Example 1.

The product was hydrogenated according to the method in Example 7 to convert coexisting reducing saccharides such as glucose and maltose into corresponding sugar alcohol. The product, containing about 50% of saccharide derivatives of α,α-trehalose (about 6% of α-maltosyl α,α-trehalose) on a dry solid basis, is advantageously used as materials for external dermatological formulation as well as Example 1. Since the product shows no reducibility, it is particularly suitable as materials for external dermatological formulations comprising ingredients inactivated by Maillard reaction.

Example 9

Thirty three percent of starch suspension was admixed with calcium carbonate to give a final concentration of 0.1%, and adjusted to pH 6.0. The resulting solution was admixed with 0.2%/g-starch on a dry solid basis of "TERMAMYL 60L", an α-amylase commercialized by NovoZyme A/S, Bagsværd, Denmark, and followed by the enzymatic reaction at 95° C. for 15 minutes. After autoclaved at 120° C. for 30 minutes, the reaction mixture was cooled to 50° C., admixed with 500 units/g-starch of isoamylase, commercialized by Hayashibara Biochemical Laboratories Inc., Okayama, Japan and 1.8 units/g-starch of maltohexaose maltoheptaose producing amylase, and followed by the enzymatic reaction for 40 hours. The reaction mixture was autoclaved at 120° C. for 10 minutes, cooled to 53° C., adjusted to pH 5.7, and admixed with 2 units/g-starch of non-reducing saccharide-forming enzyme originated from *Arthrobacter* sp. S34 (FREM BP-6450), disclosed in Japanese Patent Publication (Kokai) No. 228,980/00, and followed the enzymatic reaction for 64 hours. The reaction mixture was kept at 95° C. for 10 minutes, cooled and filtered to obtain a filtrate. According to the conventional manner, the resulting filtrate was decolored with activated charcoal, desalted and purified with ion exchangers in H- and OH-forms, and concentrated to prepare a syrup containing saccharide derivatives of α,α-trehalose. Further, the syrup was spray-dried to obtain an amorphous powder as a moisture variation inhibiting agent in a yield of about 87% to the material starch on a dry solid basis. The product contains 8.2% of α-glucosyl α,α-trehalose, 6.5% of α-maltosyl α,α-trehalose, 5.6% of α-maltotriosyl α,α-trehalose, and 21.9% of α-maltotetraosyl α,α-trehalose, 9.3% of α-maltopentaosyl α,α-trehalose, and 14.1% of α-glycosyl α,α-trehalose having eight glucose residues or more. Since the product shows a low hygroscopicity and a satisfactory solubility in water, it is advantageously used as materials for external dermatological formulation, if necessary, it is further purified according to a usual manner for the purpose of increasing the content of saccharide derivatives of α,α-trehalose.

The product was hydrogenated according to the method in Example 7 to convert coexisting reducing saccharides such as glucose and maltose into corresponding sugar alcohol, purified, and concentrated to obtain a syrup containing saccharide derivatives of α,α-trehalose and sugar alcohols such as sorbitol and maltitol. Further, the syrup was spray-dried to prepare an amorphous powder in a usual manner. The product, containing about 6% of α-maltosyl α,α-trehalose and about 59% of other saccharide derivatives of α,α-trehalose on a dry solid basis, has a low hygroscopicity and satisfactory water-solubility, even if further purified to increase the content of saccharide derivatives of α,α-trehalose, and advantageously used as materials for external dermatological formulations as well as Example 1. Since the product shows no reducibility, it is particularly suitable for external dermatological formulations comprising ingredients inactivated by Maillard reaction.

Example 10

Seventy parts by weight of the powder, containing saccharide derivatives of α,α-trehalose, prepared in Example 2, was admixed with 30 parts by weight of "MABIT®", an anhydrous crystalline maltitol commercialized by Hayashibara Shoji Inc., Okayama, Japan, to obtain a powdery mixture. The product is advantageously used as materials for external dermatological formulations.

Example 11

Seventy parts by weight of the powder, containing saccharide derivatives of α,α-trehalose, prepared in Example 7, was admixed with two parts by weight of "AA2G®", an L-ascorbic acid 2-glucoside commercialized by Hayashibara Biochemical Laboratories, Inc., Okayama, Japan and two parts by weight of "αG RUTIN", a glycosyl rutin commercialized by Hayashibara Biochemical Laboratories, Inc., Okayama, Japan, to obtain a powdery mixture. The saccharide derivatives of α,α-trehalose contained in the product enhance the effect of the substances having blood flow-promoting effect and/or antiinflammatory effect. In addition, since the saccharide derivatives of α,α-trehalose and/or glycosyl rutin inhibit the oxidation, decomposition and denaturation of co-existing ingredients such as base ingredients for external dermatological formulations, substances having emulsifying effect, perfumeries, colorants, tannin liquids, honey, beewax, propolis and amino acids, they inhibit the production of browning, discoloration and foreign smell. Therefore, the product is advantageously used as materials for external dermatological formulations.

Example 12

Seventy parts by weight of the powder, containing saccharide derivatives of α,α-trehalose, prepared in Example 7, was admixed with two parts by weight of "AA2G®" an L-ascorbic acid 2-glucoside commercialized by Hayashibara Biochemical Laboratories, Inc., Okayama, Japan and two parts by weight of "αG HESPERIDIN, a glycosyl hesperidin commercialized by Hayashibara Biochemical Laboratories, Inc., Okayama, Japan, to obtain a powdery mixture. The saccharide derivatives of α,α-trehalose contained in the product enhance the effect of the substances having blood flow-promoting effect and/or antiinflammatory effect. In addition, since the saccharide derivatives of α,α-trehalose and/or glycosyl hesperidin inhibit the oxidation, decomposition and denaturation of co-existing ingredients such as base ingredients for external dermatological formulations, substances having emulsifying effect, perfumeries, colorants, tannin liquids, honey, beeswax, propolis and amino acids, they inhibit the browning, discoloration and generation of foreign smell. Therefore, the product is advantageously used as materials for external dermatological formulations.

Example 13

Eighty parts by weight of the syrup containing saccharide derivatives of α,α-trehalose, prepared in Example 6, and 20 parts by weight of hydrous crystalline trehalose (reagent grade, purity 99.0% or more) commercialized by Hayashibara Biological Laboratories Inc., Okayama, Japan, were mixed together to prepare a syrup. The product is advantageously used as materials for external dermatological formulation.

Example 14

Cosmetic Soap 96.5 parts by weight of a neat soup, prepared by saponifying tallow and palm oil in the rate of 4:1 by weight, and salting out in a usual manner, was admixed with 1.5 parts by weight of the powder containing saccharide derivatives of α,α-trehalose, prepared in Example 3, 0.5 part by weight of "AA2G®", an L-ascorbic acid 2-glucoside commercialized by Hayashibara Biochemical Laboratories, Inc., Okayama, Japan, 0.5 part by weight of sucrose, 0.5 part by weight of "αG RUTIN", a glycosyl rutin commercialized by Hayashibara Biochemical Laboratories, Inc., Okayama, Japan, one part by weight of maltitol, 0.0001 part by weight of Kanko-so No. 201, and an appropriate amount of perfumeries, and mixed gently. The resultant was poured into molds, cooled and solidified to obtain a soap. The product is a soap having a whitening effect due to L-ascorbic acid 2-glucoside, and has a satisfactory skin feeling without desiccating after used. Since the product is inhibited in the oxidation, decomposition and denaturation of base ingredients for soaps, substances having emulsifying effect, perfumeries or colorants by the saccharide derivatives of α,α-trehalose and/or glycosyl rutin, they are inhibited in the browning, discoloration and the generation of foreign smell in a long period. Therefore, the product keeps to have a high quality for a long period. In addition, the product is a transparent soap, which is improved in the problem of conventional soaps containing saccharides, such as cloud and yellowing, because of containing the saccharide derivatives of α,α-trehalose.

Example 15

Face Wash

Ten parts by weight of trehalose monomyristate, one part by weight of glyceryl dioleate, 15 parts by weight of myristinic acid, five parts by weight of liquid paraffin, eight parts by weight of glycerin, four parts by weight of the syrupy saccharide derivatives of α,α-trehalose, prepared in Example 6, 0.2 part by weight of methyl paraoxybenzoate, 0.1 part by weight of edetate salts, 0.8 part by weight of glycyrrhizin, 0.4 part by weight of potassium hydroxide, 15 parts by weight of N-methyl-2-prrolidone, and an appropriate amount of citrus flavor were mixed and admixed with water to give a final weight of 100 parts in order to obtain a face wash. The product, enhanced in the antiinflammatory effect of glycyrrhizin by the saccharide derivatives of α,α-trehalose, is a face wash having a satisfactory moisturizing effect and skin feeling without sticky feeling after used.

Example 16

Bath Salt

Forty four parts by weight of sodium sulfate, 14 parts by weight of sodium bicarbonate, seven parts by weight of sodium carbonate, 21 parts by weight of succinic acid, five parts by weight of the powder containing saccharide derivatives of α,α-trehalose, prepared in Example 7, and an appropriate amount of lubricant, colorants and perfumeries were mixed homogeneously, and tableted to obtain a bath salt. The product produces carbonic acid gas having blood flow-promoting effect when entered into bathtub. It is a bath salt having a satisfactory skin feeling without sticky feeling after used.

Example 17

Bath Salt

Forty parts by weight of sodium sulfate, 26 parts by weight of sodium bicarbonate, 20 parts by weight of sodium carbonate, five parts by weight of "αG HESPERIDIN", a glycosyl hesperidin commercialized by Hayashibara Shoji, Inc., Okayama, Japan, 7.5 parts by weight of the powder containing saccharide derivatives of α,α-trehalose, prepared in Example 2, 2.5 parts by weight of "Trehalose", a crystalline hydrous trehalose commercialized by Hayashibara Biochemical Laboratories, Inc., Okayama, Japan, and an appropriate amount of perfumeries were mixed homogeneously to obtain a powdery bath salt. The product has a satisfactory blood flow-promoting effect due to the glycosyl hesperidin, and is a bath salt having a satisfactory skin feeling without sticky feeling after used. When the product was used by seven panels with atopic diseases, it got the answers from all seven panels that it improved the symptoms of atopic diseases.

Example 18

Eye Shadow 6.0 parts by weight of talc, 10.0 parts by weight of "Trehalose", an α,α-trehalose commercialized by Hayashibara Biochemical Laboratories, Okayama, Japan, five parts by weight of the powder containing saccharide derivatives of α,α-trehalose, prepared in Example 7, 60.0 parts by weight of muscovite, 8.0 parts by weight of ultramarine, 3.0 parts by weight of yellow iron oxide, 1.0 part by weight of black iron oxide and 0.1 part by weight of indomethacin were mixed together by a henschel mixer. To the resultant was sprayed seven parts by weight of a heat-dissolved mixture containing 4.0 parts by weight of squalane, 1.9 parts by weight of cetyl 2-ethylhexanoate, 0.8 part by weight of sorbitan sesquioleate, 0.1 part by weight of antiseptics and 0.2 part by weight of colorants and mixed together. The resultant was pulverized and placed into inner containers to obtain an eye shadow. The product has a satisfactory antiinflammatory effect due to indomethacin and hardly causes dermatitis even if contacted with skins. The product is capable of freshly making up and satisfactorily keeping the makeup by moisturizing effect of saccharide derivatives of α,α-trehalose.

Example 19

Brusher 12.6 parts by weight of talc, 74.9 parts by weight of sericite, 0.2 part by weight of the powder containing saccharide derivatives of α,α-trehalose, prepared in Example 7, 0.1 part by weight of ultramarine, 0.4 part by weight of yellow iron oxide, 0.4 part by weight of red iron oxide, 0.4 part by weight of Red No. 226, and 0.1 part by weight of azulene were mixed together by a henschel mixer. To the resultant was sprayed 8.4 parts by weight of a heat-dissolved mixture containing 3.0 parts by weight of squalane, 5.0 parts by weight of 2-ethylhexyl palmitate, 0.3 part by weight of antiseptics and 0.1 part by weight of perfumeries and mixed together. The resultant was pulverized, admixed with 3.0 parts by weight of titan mica and placed into inner containers to obtain a brusher. The product has a satisfactory antiinflammatory effect due to azulene and hardly causes dermatitis even if contacted with skins. The product is capable of freshly making up and satisfactorily keeping the makeup by moisturizing effect of saccharide derivatives of α,α-trehalose Example 20

Powder Foundation 2.0 parts by weight of titanium oxide, 10.0 parts by weight of talc, 3.0 parts by weight of muscovite, 55.0 parts by weight of sericite, three parts by weight of the powder containing saccharide derivatives of α,α-trehalose, prepared in Example 7, 1.0 part by weight of "Trehalose", an α,α-trehalose commercialized by Hayashibara Biochemical Laboratories, Inc., Okayama, Japan, 12.0 parts by weight of nylon powder, 0.5 part by weight of red iron oxide, 1.0 part by weight of yellow iron oxide, 0.1 part by weight of black iron oxide, and 0.1 part by weight of allantoin were mixed by a henschel mixer. To the resultant was added a heat-resolved mixture containing 1.0 part by weight of silicon oil, 9.0 part by weight of ethyl hexyl palmitate, 2.0 parts by weight of the powder containing saccharide derivatives of α,α-trehalose, prepared in Wxample 7, 1.0 part by weight of sorbitan sesquioleate, 0.3 part by weight of antiseptics and 0.1 part by weight of perfumeries and mixed. The resultant was pulverized and placed into inner containers to obtain a powder foundation. The product has a satisfactory antiinflammatory effect due to allantoin and hardly causes dermatitis even if contacted with skins. The product is capable of freshly making up and satisfactorily keeping the makeup by moisturizing effect of saccharide derivatives of α,α-trehalose and has a satisfactory skin feeling without sticky feeling.

Example 21

Foundation 3.5 parts by weight of cetanol, four parts by weight of deodorized lanolin, five parts by weight of jojoba oil, two parts by weight of vaseline, six parts by weight of squalane, 2.5 parts by weight of monoglyceryl stearate, 1.5 parts by weight of polyoxyethylene(60) caster wax, one part by weight of polyoxyethylene(25) cetyl ether, 0.2 part by eight of γ-oryzanol, 0.2 part by weight of perfumeries, three parts by weight of glycerin, eight parts by weight of propylene glycol, 12 parts by weight of a preparated powder, three parts by weight of allantoin, three parts by weight of the syrup containing saccharide derivatives of α,α-trehalose, prepared in Example 6, an appropriate amount of ion-exchange water to give a final weight of 100 parts in order to obtain a foundation. The product, enhanced in the antiphlogistic effect of γ-oryzanol by the saccharide derivatives of α,α-trehalose, is a foundation having a satisfactory skin feeling without sticky feeling after used.

Example 22

Absorption Ointment

Forty parts by weight of vaseline, 15 parts by weight of stearyl alcohol, 15 parts by weight of Japan wax, 15 parts by weight of polyethylene(10) oleate, 0.25 part by weight of monoglyceryl stearate, three parts by weight of pantothenyl alcohol, 3.0 parts by weight of the syrup containing saccharide derivatives of α,α-trehalose, prepared in Example 6, and an appropriate deionized water were mixed together in a usual manner to obtain an absorption ointment. The product, enhanced in the antiphlogistic effect of pantothenyl alcohol by the saccharide derivatives of α,α-trehalose, is an absorption ointment having a satisfactory skin feeling without sticky feeling after used.

Example 23

Hair Tonic

Fifty parts by weight of ethanol, 1.5 parts by weight of polyoxyethylene(8) oleate, 0.1 part by weight of hinokithiol, 1.0 part by weight of glycyrrhizin, 0.01 part by weight of Kanko-so No. 301, five parts by weight of trehalose, 10 parts by weight of the syrup containing saccharide derivatives of α,α-trehalose, prepared in Example 6, 0.1 part by weight of ethylparaben, 0.05 part by weight of perfumeries, and an appropriate amount of deionized water were admixed together in a usual manner to obtain a hair tonic. The product, enhanced in the hair growing and hair nourishing effect of Kanko-so No. 301 and the antiphlogistic effect of glycyrrhizin by the saccharide derivatives of α,α-trehalose, is a hair tonic having a satisfactory skin feeling without sticky feeling after used.

Example 24

Cosmetic Cream

Two parts by weight of polyoxyethylene glycol monostearate, five parts by weight of glyceryl monostearate self-emulsifying, one part by weight of behenyl alcohol, two parts by weight of eicosatetraenoic acid, five parts by weight of liquid paraffin, 10 parts by weight of glyceryl trioctanate, and an appropriate amount of antiseptics were heat-resolved in a usual manner. The resulting mixture was admixed with two part by weight of the syrup containing saccharide derivatives of α,α-trehalose, prepared according to the method in Example 6, five parts by weight of sodium dl-lactate, five parts by weight of 1,3-butylene glycol, one part by weight of ginseng extract, and 65 parts by weight of purified water. The resulting mixture was emulsified by a homogenizer and admixed with an appropriate amount of perfumeries with stirring to obtain a cream. The product is enhanced in the blood flow-promoting effect of ginseng extract by the saccharide derivatives of α,α-trehalose, and lowered in the unpleasant smell of ingredients such as a substance having emulsifying effect. The product is a whitening cream stably keeping its high quality without browning. In addition, since the product is capable of inhibiting the oxidation and decomposition of lipid from sweat, dirt, scurf or sebum, it can be advantageously used for lowering body odor, preventing the stimulation or itch on skins, or treating or preventing chromatophathy. The product is a cream having a satisfactory skin feeling without sticky feeling when applied on skins.

Example 25

Cosmetic Cream

Two parts by weight of polyoxyethylene glycol monostearate, five parts by weight of glyceryl monostearate self-emulsifying, three parts by weight of behenyl alcohol, two parts by weight of eicosatetraenoic acid, five parts by weight of liquid paraffin, 10 parts by weight of glyceryl trioctanate, and an appropriate amount of antiseptics were mixed and heat-dissolved. The resulting mixture was admixed with 1.6 parts by weight of the syrup containing saccharide derivatives of α,α-trehalose, prepared in Example 7, two parts by weight of "AA2G®", an L-ascorbic acid 2-glucoside commercialized by Hayashibara Biochemical Laboratories, Inc., Okayama, Japan, 0.1 part by weight of sodium hyaluronate, 0.1 part by weight of dipotassium glycyrrhizinate, 0.1 part by weight of aloe extract, 0.05 part by weight of balm mint extract, 0.05 part by weight of chamomile extract, 0.5 part by weight of "αG HESPERIDIN", a glycosyl hesperidin commercialized by Hayashibara Biochemical Laboratories, Inc., Okayama, Japan, one part by weight of indigo ethanol extract, five parts by weight of sodium dl-lactate, five parts by weight of 1,3-butylene glycol, and 66 parts by weight of purified water, and emulsified by homogenizer. The resulting emulsion was admixed with an appropriate amount of perfumeries with stirring to obtain a cream. The product, enhanced in the blood flow-promoting effect of glycyrrhizinic acid, glycosyl hesperidin and/or indigo ethanol extract by the saccharide derivatives of α,α-trehalose, is advantageously used for preventing the stimulation or itch on skins, or treating or preventing chromatophathy such as liver spot, freckling and sunburn, and aging of skins. Since the product has a low stimulation against skins and a satisfactory moisturizing effect given by the saccharide derivatives of α,α-trehalose contained therein, it can be used without care of hypersensitivity. The product is a cream having a satisfactory skin feeling without sticky feeling when applied on skins.

Example 26

Cosmetic Cream

Three parts by weight of polyglyceryl(10) stearate, 0.5 part by weight of stearyl alcohol, three parts by weight of behenyl alcohol, one part by weight of butylalcohol, one part by weight of cetyl palmitate, one part by weight of glyceryl stearate, one part by weight of fatty acid (C10-30, cholesteryl/lanosteryl), four parts by weight of isopropyl palmitate, five parts by weight of squalane, five parts by weight of octyldodecyl myristate, 0.5 part by weight of Macadamia nut oil, 1.8 parts by weight of trioctanoin, 0.3 part by weight of dimethicone, six parts by weight of 1,3-butylene glycol, 2.5 parts by weight of pentylene glycol, 0.1 part by weight of dipotassium glycyrrhizinate, five parts by weight of the syrup containing saccharide derivatives of α,α-trehalose at a concentration of 75%, on a dry solid basis, prepared in Example 6, five parts by weight of concentrated glycerin, 15.63 parts by weight of a solution comtaining two parts by weight of ascorbic acid 2-glucoside, 2.33 parts by weight of 10% aqueous solution of sodium hydroxide, one part by weight of 10% aqueous solution of sodium citrate and 10 parts by weight of purified water, and 37.62 parts by weight of purified water were admixed together to obtain a cream. The cream was prepared by emulsifying in the manner of heating with stirring at 4,000 rpm for five minutes using homomixer and cooling with stirring. The product, enhanced in the antiinflammatory effect of glycyrrhizinic acid by the saccharide derivatives of α,α-trehalose, is advantageously used for preventing the stimulation or itch on skins, or treating or preventing chromatophathy such as liver spot, freckling and sunburn, and aging of skins. The saccharide derivatives of α,α-trehalose contained therein enable to easily emulsify and improve the working efficiency to produce a cream even if containing ascorbic acid 2-glucoside. In addition, since the product has a low stimulation against skins and a satisfactory moisturizing effect, it can be used without care of hypersensitivity. The product is a cream having a satisfactory skin feeling without sticky feeling when applied on skins.

A cream was produced by the same method in Example 26 except for admixing five parts by weight of concentrated glycerin instead of five parts by weight of the syrup containing saccharide derivatives of α,α-trehalose. 0.15 part by weight of this cream or the cream prepared in Example 26 was admixed with 99.85 parts by weight of purified water with stirring for five minutes. Each resulting solution was placed in a cell for measurement of particle size and subjected to the measurement of emulsifying particle distribution using "SA-CP3L", a centrifugal sedimentation particle size distribution measuring instrument commercialized by Shimazu Corporation, Kyoto, Japan. The result was shown in Table 15.

TABLE 15

| | Rate of the particle size distribution (%) | |
|---|---|---|
| Particle size (μm) | Cream containing base ingredient | Cream containing saccharide derivatives of α,α-trehalose |
| 300–200 | 8.3 | 1.4 |
| 200–100 | 27.0 | 4.5 |
| 100–50 | 0 | 0 |
| 50–20 | 4.4 | 9.3 |
| 20–10 | 29.3 | 33.4 |
| 10–5 | 25.2 | 44.7 |
| 5–2 | 4.6 | 5.1 |
| 2 or less | 1.1 | 1.5 |
| Median of Particle size (μm) | 16.5 | 9.9 |

As evidence from the result in Table 15, the particles sized with 2-20 μm occupied about 83% of the total particles in the cream containing the syrup containing saccharide derivatives of α,α-trehalose. The particles sized with 100 μm or more slightly occupied about 15% of the total particles. The median of particle size was 9.9 μm. In contrast, the particles sized 100 μm or more occupied about 35% of the total particles in the cream containing concentrated glycerin without saccharide derivatives of α,α-trehalose. The median of particle size was 16.5 μm. As a result, saccharide mixture containing saccharide derivatives of α,α-trehalose was capable of producing a cream having uniform and small particles than glycerin. Microscopic observation of the emulsion state showed the same result to the measurement of particle size distribution, although photographic evidence was not shown.

Example 27

Cosmetic Cream

Two parts by weight of polyoxyethylene glycol monostearate, five parts by weight of glyceryl monostearate self-emulsifying, three parts by weight of behenyl alcohol, two parts by weight of eicosatetraenoic acid, five parts by weight of liquid paraffin, 10 parts by weight of glyceryl trioctanate, and an appropriate amount of antiseptics were mixed and heat-dissolved. The resulting mixture was admixed with 2.6 parts by weight of the syrup containing saccharide derivatives of α,α-trehalose, prepared in Example 6, two parts by weight of "AA2G®", an L-ascorbic acid 2-glucoside commercialized by Hayashibara Biochemical Laboratories, Inc., Okayama, Japan, 1.5 parts by weight of "αG RUTIN", a glycosyl rutin commercialized by Hayashibara Biochemical Laboratories, Inc., Okayama, Japan, 0.1 part by weight of sodium hyaluronate, 0.1 part by weight of dipotassium glycyrrhizinate, 0.1 part by weight of aloe extract, 0.05 part by weight of balm mint extract, 0.05 part by weight of chamomile extract, one part by weight of indigo ethanol extract, 0.5 part by weight of EDTA 2Na, 4.5 parts by weight of sodium dl-lactate, five parts by weight of 1,3-butylene glycol, and 66 parts by weight of purified water, and emulsified by homogenizer. The resulting emulsion was admixed with an appropriate amount of perfumeries with stirring to obtain a cream. The product, enhanced in the blood flow-promoting effect of glycyrrhizinic acid and/or indigo ethanol extract by the saccharide derivatives of α,α-trehalose, is advantageously used for preventing the stimulation or itch on skins, or treating or preventing chromatophathy such as liver spot, freckling and sunburn, and aging of skins. Since the product has a low stimulation against skins and a satisfactory moisturizing effect given by the saccharide derivatives of α,α-trehalose, it can be used without care of hypersensitivity. The product is a cream having a satisfactory skin feeling without sticky feeling when applied on skins. The saccharide derivatives of α,α-trehalose, EDTA-2Na as a chelating agent, dl-sodium lactate and glycosyl rutin inhibit the oxidation, decomposition and denaturation of base ingredients for soaps, substances having emulsifying effect, perfumeries or colorants, they inhibit the browning, discoloration and generation of foreign smell in a long period. Therefore, the product keeps its quality for a long period.

Example 28

Cosmetic Cream

Forty five parts by weight of purified water, four parts by weight of the syrup containing saccharide derivatives of α,α-trehalose, prepared in Example 6, 1.5 parts by weight of 1,3-butylene glycol as a stickening agent, 2.5 parts by weight of "Sepigel 305", a polymer composed by polyacrylamide, C13-C14 isoparaffin and raures-7 commercialized by Shibahashi Chemifa, Co., Ltd., Tokyo, Japan, were mixed with stirring in an ambient temperature. Fifty three parts by weight of the resulting mixture was gradually admixed with a heat-melted mixture containing 1.5 parts by weight of squalane, two parts by weight of isopropyl palmitate, 1.5 parts by weight of octyldodecyl myristate, 1.5 parts by weight of jojoba oil, one part by weight of silicon and 0.15 part by weight of methylparaben in a manner of heating to 80° C. and cooling to 55° C. in order to prepare an oily phase mixture. 60.65 parts by weight of the oily phase mixture was gradually admixed with aqueous phase mixture prepared by mixing 0.05 part by weight of glycyrrhizinic acid dissolved in 29.8 parts by weight of purified water, one part by weight of 1,3-butylene glycol, 2.5 parts by weight of 1,2-pentandiol and six parts by weight of concentrated glycerin together, and stirred in a usual manner to obtain a cream. The product, enhanced in the antiinflammatory effect of glycyrrhizinic acid by the saccharide derivatives of α,α-trehalose, is advantageously used for preventing the stimulation or itch on skins, or treating or preventing chromatophathy such as liver spot, freckling and sunburn, and aging of skins. The manner of dissolving in combination of saccharide derivatives of α,α-trehalose and gums as this example improves the water-solubility of the gums and enables to more efficiently produce cosmetic creams than the manner of dissolving the saccharide derivatives of α,α-trehalose within aqueous phase ingredients.

Example 29

Night Cream

Four parts by weight of cetanol, seven parts by weight of vaseline, 21 parts by weight of squalane, 2.2 parts by weight of monoglyceryl stearate, 2.8 parts by weight of polyoxyethylene(20) sorbitan monostearate, six parts by weight of isopropyl myristate, 0.3 part by weight of ethylparaben, 0.2 part by weight of perfumeries, 10 parts by weight of propylene glycol, five parts by weight of 1,3-butylene glycol, 0.1 part by weight of glycyrrhetin, three parts by weight of the powder containing saccharide derivatives of α,α-trehalose, prepared in Example 7, and an appropriate amount of deionized water to give a final weight of 100 parts in order to obtain a night cream. The product, enhanced in the antiinflammatory effect of glycyrrhetin by the saccharide derivatives of α,α-trehalose, is advantageously used for preventing rough skins, stimulation or itch on skins. Since the product has a low stimulation against skins and a satisfactory moisturizing effect given by the saccharide derivatives of α,α-trehalose, it can be used without care of hypersensitivity. The product is a cream having a satisfactory skin feeling without sticky feeling when applied on skins.

Example 30

Hand Cream 20.0 parts by weight of the syrup containing saccharide derivatives of α,α-trehalose, prepared in Example 6, 2.0 parts by weight of urea, 2.5 parts by weight of POE(60) glyceryl isostearate, 1.5 parts by weight of monoglyceryl stearate, four parts by weight of cetanol, 2.0 parts by weight of vaseline, 10 parts by weight of liquid paraffin, 0.01 part by weight of 2-ethylhexyl-4-tetra-butyl-4-methoxybenzoylmethane paraoxycinnamate, 0.2 part by weight of vitamin E acetate, 0.1 part by weight of vitamin D and an appropriate amount of purified water to give a final weight of 100 parts in order to a hand cream. The product, enhanced in the blood flow-promoting effect and/or antiinflammatory effect of vitamin E acetate by the saccharide derivatives of α,α-trehalose, is advantageously used for preventing rough skins, stimulation or itch on skins and preventing a damage by UV. Since the product has a low stimulation against skins and a satisfactory moisturizing effect given by the saccharide derivatives of α,α-trehalose, it can be used without care of hypersensitivity. The product is a cream having a satisfactory skin feeling without sticky feeling when applied on skins.

Example 31

Milky Lotion 2.5 parts by weight of stearic acid, 1.5 parts by weight of cetanol, five parts by weight of vaseline, 10 parts by weight of liquid paraffin, two parts by weight of polyoxyethylene oleate, 0.5 parts by weight of tocopherol acetate, 0.2 part by weight of dipotassium glycyrrhizinate, three parts by weight of polyethylene glycol(1500), three parts by weight of ethyl L-ascorbate, three parts by weight of indigo aqueous extract, two parts by weight of arbutin, one part by weight of "αG RUTIN", a glycosyl rutin commercialized by Hayashibara Biochemical Laboratories, Inc., Okayama, Japan, one part by weight of triethanolamine, two parts by weight of the syrup containing saccharide derivatives of α,α-trehalose, prepared in Example 6, 66 parts by weight of purified water and 0.1 part by weight of propylparaben were mixed together, adjusted to pH 6.7 with potassium hydroxide, and admixed an appropriate amount of perfumeries in a usual manner to obtain a milky lotion. The product, enhanced in the antiinflammatory effect of indigo aqueous extract by the saccharide derivatives of α,α-trehalose, is advantageously used for alleviating or preventing inflammatory symptom such as stimulation or itch on skins, treating or preventing aging of skins. Since the product has a low stimulation against skins and a satisfactory moisturizing effect given by the saccharide derivatives of α,α-trehalose, it is a cream having a satisfactory skin feeling without sticky feeling when applied on skins.

Example 32

Milky Lotion 2.5 parts by weight of stearic acid, 1.5 parts by weight of cetanol, five parts by weight of vaseline, 10 parts by weight of liquid paraffin, two parts by weight of polyoxyethylene(10) oleate, 0.1 part by weight of propylparaben, 0.5 part by weight of dl-α-tocopherol acetate, 0.2 part by weight of perfumeries, three parts by weight of polyoxyethylene glycol (1500), one part by weight of triethanolamine, two parts by weight of "AA2G®", an L-ascorbic acid 2-glucoside commercialized by Hayashibara Biochemical Laboratories, Inc., Okayama, Japan, two parts by weight of the syrup containing saccharide derivatives of α,α-trehalose, prepared in Example 6, and appropriate amount of deionized water to give a final weight of 100 parts in order to obtain a milky lotion. The product, enhanced in the blood flow-promoting effect of dl-α-tocopherol acetate by the saccharide derivatives of α,α-trehalose, is advantageously used for preventing the stimulation or itch on skins, or treating or preventing chromatophathy such as liver spot, freckling and sunburn, and aging of skins. Since the product has a satisfactory moisturizing effect given by the saccharide derivatives of α,α-trehalose, it is a cream having a satisfactory skin feeling without sticky feeling when applied on skins.

Example 33

Skin Lotion 0.2 part by weight of dipotassium glycyrrhizinate, 0.1 part by weight of citric acid, 0.3 part by weight of sodium citrate, 2.0 parts by weight of the syrup containing saccharide derivatives of α,α-trehalose, prepared in Example 6, 5.0 parts by weight of ethanol, 0.0001 part by weight of Kanko-so No. 201, 0.1 part of ethylparaben and an appropriate amount of water to give a final weight of 100 parts were mixed together to obtain a skin lotion. The product, enhanced in the antiphlogistic effect of glycyrrhizinic acid by the saccharide derivatives of α,α-trehalose, is advantageously used for preventing rough skins, stimulation or itch on skins. Since the product has a low stimulation against skins and a satisfactory moisturizing effect given by the saccharide derivatives of α,α-trehalose, it can be used without care of hypersensitivity. The product is a cream having a satisfactory skin feeling without sticky feeling when applied on skins.

Example 34

Cosmetic Essence 0.5 part by weight of polyoxyethylene sorbitol tetraoleate, 1.0 part by weight of squalane, 0.3 part by weight of xanthane gum, 0.2 part by weight of hydroxyethylcellulose, 3.0 parts by weight of the syrup containing saccharide derivatives of α,α-trehalose, prepared in Example 6, 0.05 part by weight of sodium hyaluronate, 1.0 part by weight of "αG RUTIN", a glycosyl rutin commercialized by Hayashibara Biochemical Laboratories, Inc., Okayama, Japan, 0.1 part by weight of disodium edetate, 0.5 part by weight of indigo aqueous extract, 0.1 part by weight of ethylparaben, and appropriate amount of water to give a final weight of 100 parts were mixed and dissolved together in a usual manner to obtain a cosmetic essence. The product, enhanced in the antiinflammatory effect of indigo aqueous extract by the saccharide derivatives of α,α-trehalose, is advantageously used for preventing rough skins, stimulation or itch on skins, and treating and preventing aging of skins. Since the product has a low stimulation against skins and a satisfactory moisturizing effect given by the saccharide derivatives of α,α-trehalose, it is a cream having a satisfactory skin feeling without sticky feeling when applied on skins. The saccharide derivatives of α,α-trehalose and/or glycosyl rutin inhibit the oxidation, decomposition and denaturation of co-existing base ingredients for external dermatological formulation, substances having emulsifying effect, perfumeries or colorants, they inhibit the browning, discoloration and generation of foreign smell in a long period. Therefore, the product keeps its quality for a long period.

Example 35

Cosmetic Essence 0.5 part by weight of polyoxyethylene sorbitol tetraoleate, 1.0 part by weight of squalane, 0.3 part by weight of xanthane gum, 0.2 part by weight of hydroxyethylcellulose, 3.0 parts by weight of the syrup containing saccharide derivatives of α,α-trehalose, prepared in Example 6, two parts by weight of L-ascorbic acid, 0.05 part by weight of sodium hyaluronate, 1.0 part by weight of "αG RUTIN", a glycosyl rutin commercialized by Hayashibara Biochemical Laboratories, Inc., Okayama, Japan, 1.0 part by weight of "αG HESPERIDIN", a glycosyl hesperidin commercialized by Hayashibara Biochemical Laboratories, Inc., Okayama, Japan, 0.1 part by weight of disodium edetate, 0.5 part by weight of indigo aqueous extract, 0.1 part by weight of ethylparaben, and appropriate amount of water to give a final weight of 100 parts were mixed and dissolved together, and adjusted to about pH 6.8 with potassium hydroxide in a usual manner to obtain a cosmetic essence. The product, enhanced in the antiinflammatory effect of indigo aqueous extract and blood flow-promoting effect of glycosyl rutin and glycosyl hesperidin by the saccharide derivatives of α,α-trehalose, is advantageously used for preventing rough skins, stimulation or itch on skins, and treating and preventing aging of skins. Since the product has a low stimulation against skins and a satisfactory moisturizing effect given by the saccharide derivatives of α,α-trehalose, it is a cosmetic essence having a satisfactory skin feeling without sticky feeling when applied on skins. The saccharide derivatives of α,α-trehalose and/or glycosyl rutin inhibit the oxidation, decomposition and denaturation of it or substances having emulsifying effect and perfumeries, they inhibit the browning, discoloration and generation of foreign smell. Therefore, the product is inhibited in the deterioration of quality for a long period.

Example 36

Lotion

Twenty parts by weight of 1% sodium hyaluronate aqueous solution, two parts by weight of the saccharide derivatives of α,α-trehalose, prepared in Example 6, 2.1 parts by weight of 60% sorbitol aqueous solution, 0.5 part by weight of glycyrrhiza extract, 0.05 part by weight of chamomile extract, 1.0 part by weight of sage extract, 0.001 part by weight of aloe extract powder, 0.02 part by weight of citric acid, 0.18 part by weight of sodium citrate, 0.05 part by weight of methyl paraoxybenzoate and an appropriate amount of water to give a final weight of 100 parts were mixed together to obtain a lotion. The product, enhanced in the antiphlogistic effect of glycyrrhiza extract by the saccharide derivatives of α,α-trehalose, is advantageously used for preventing rough skins, stimulation or itch on skins, and treating and preventing aging of skins. Since the product has a low stimulation against skins and a satisfactory moisturizing effect given by the saccharide derivatives of α,α-trehalose, it is a lotion having a satisfactory skin feeling without sticky feeling when applied on skins.

Example 37

Mudpack 9.0 parts by weight of bentonite, 14.0 parts by weight of kaolin, 1.0 part by weight of polyoxyethylene sorbitan monostearate, 10.0 parts by weight of the syrup containing saccharide derivatives of α,α-trehalose, prepared in Example 6, 0.35 part by weight of dipotassium glycyrrhizinate, 3.0 parts by weight of indigo aqueous extract, 0.1 part by weight of ethylparaben, 5.0 parts by weight of ethanol, 10.0 parts by weight of polyethylene glycol, and 47.5 parts by weight of water were heated and homogeneously mixed together to obtain a mudpack. The product, enhanced in the antiphlogistic effect of glycyrrhizinic acid by the saccharide derivatives of α,α-trehalose, is advantageously used for preventing rough skins, stimulation or itch on skins, and treating and preventing aging of skins. Since the product has a low stimulation against skins and a satisfactory moisturizing effect given by the saccharide derivatives of α,α-trehalose, it is a lotion having a satisfactory skin feeling without sticky feeling when applied on skins.

Example 38

Gel Cream for Sun-protect 4.0 parts by weight of octyl paramethoxy cinnamate, 3.0 parts by weight of oxybenzon, 16.0 parts by weight of liquid paraffin, 9.0 parts by weight of olive oil and 0.01 part by weight of dibutylhydroxytoluene were heated and mixed together, and admixed with 1.0 part by weight of the syrup containing saccharide derivatives of α,α-trehalose, prepared in Example 6, 0.6 part by weight of acrylic acid/alkyl methacrylate co-polymer, 0.4 part by weight of carboxyvinylpolymer, 2.0 parts by weight of "AA2G®", an L-ascorbic acid 2-glucoside commercialized by Hayashibara Biochemical Laboratories, Inc., Okayama, Japan, 1.0 part by weight of allantoin, 1.0 part by weight of triethanolamine, and appropriate amounts of antiseptics and water to give a final weight of 100 parts, and emulsified in a usual manner to obtain a cream. The product, enhanced in the antiinflammatory effect of allantoin by the saccharide derivatives of α,α-trehalose, is a gel having a satisfactory antiphlogistic effect to prevent sunburn and alleviating burning. Since the product has a satisfactory moisturizing effect given by the saccharide derivatives of α,α-trehalose, it has a satisfactory skin feeling without sticky feeling when applied on skins. The product, lowered in the stimulation against skins by the effect of saccharide derivatives of α,α-trehalose, gives a relatively-low pain to skins even when applied to sunburned skin. It prevents aging of skins due to UV, and is a gentle gel cream to skins.

Example 39

Gel for Sun-rotect 1.0 part by weight of "AQUPEC HV505", a polyacrylate type polymer commercialized by Sumitomo Seika Chemicals Co., Ltd., Osaka, Japan, dispersed in an appropriate amount of purified water heated at about 55° C. and cooled to below 40° C., was admixed with 2.0 parts by weight of "AA2G®", an L-ascorbic acid 2-glucoside commercialized by Hayashibara Biochemical Laboratories, Inc., Okayama, Japan, dissolving in an appropriate amount of water, and further admixed with 0.9 part by weight of potassium-hydroxide to be adjusted to pH6.3. The resulting mixture was admixed with 2.0 parts by weight of saccharide derivatives of α,α-trehalose, prepared in Example 6, 4.0 parts by weight of concentrated glycerin, 2.0 parts by weight of 1,3-butylene glycol, 3.0 parts by weight of dipropylene glycol, two parts by weight of "αG HESPERIDIN", a glycosyl hesperidin commercialized by Hayashibara Biochemical Laboratories, Inc., Okayama, Japan, 1.3 parts by weight of sorbitol, 1.5 parts by weight of polyethylene glycol(400), 3.1 parts by weight of 1,2-pentanediol and 0.5 part by weight of glycyrrhetinic acid, dissolved, and further admixed with purified water to give a final weight of 100 parts in order to obtain a gel for sun-protect. The product, enhanced in the antiinflammatory effect of glycyrrhetinic acid and L-ascorbic acid 2-glucoside by the saccharide derivatives of α,α-trehalose, is a gel having a satisfactory antiphlogistic effect to prevent sunburn and alleviating burning. Since the product has a satisfactory moisturizing effect given by the saccharide derivatives of α,α-trehalose, it has a satisfactory skin feeling without sticky feeling when applied on skins. In addition, the product, containing dipropylene glycol and polyethylene glycol, is kept at pH 5.9-7.0 by adding potassium hydroxide. The product is a transparent gel having a satisfactory skin feeling without occurrence of kink or dirt characteristic to the gel containing L-ascorbic acid 2-glucoside. The product is a so stable gel that it does not show the change of pH, reduction of viscosity, and coloring even when preserved for a long period. The product, lowered in the stimulation against skins by the effect of saccharide derivatives of α,α-trehalose, gives a relatively-low pain to skins even when applied to sunburned skin. It prevents aging of skins due to UV, and is a gentle gel cream to skins.

Example 40

Gel for Preventing Aging 51.3 parts by weight of trioctalein, 16.4 parts by weight of the syrup containing saccharide derivatives of α,α-trehalose, prepared in Example 6, 14.5 parts by weight of purified water, 8.7 parts by weight of glycerol, 5.2 parts by weight of polyglyceryl(10) monomyristate, 1.75 parts by weight of polyglyceryl(10) monostearate, one part by weight of "AA2G®", an ascorbic acid 2-glucoside commercialized by Hayashibara Biochemical Laboratories, Inc., Okayama, Japan, two parts by weight of "αG RUTIN", a glycosyl rutin commercialized by Hayashibara Biochemical Laboratories, Inc., Okayama, Japan, and 0.1 part by weight of methylparaben were used in a usual manner to obtain a gel. The product, lowered in the stimulation against skins by the effect of saccharide derivatives of α,α-trehalose, gives a relatively-low pain to skins even when applied to sunburned skin. It prevents aging of skins due to UV, and is a gentle gel cream to skins.

Example 41

Cleansing Foam

A cleansing foam was produced by adding following ingredients in a usual manner; 14 parts by weight of myristic acid, nine parts by weight of palmitic acid, seven parts by weight of stearic acid, parts by weight of the syrup containing saccharide derivatives of α,α-trehalose, prepared in Example 6, three parts by weight of polyethylene glycol(4000), two parts by weight of ethylene glycol distearate, six parts by weight of polyethylene glycol distearate(140 E.O.), four parts by weight of diethanolamide laurate, 0.4 part by weight of methyl paraoxybenzoate, 0.1 part by weight of tocopherol, 6.3 parts by weight of potassium hydroxide, 30% aqueous solution of amidepropyl betaine laurate, and 26.2 parts by weight of purified water. The product, enhanced in the anti-inflammatory effect of tocopherol by the saccharide derivatives of α,α-trehalose, is a foam having a satisfactory antiphlogistic effect to prevent sunburn and alleviating burning. Since the product has a satisfactory moisturizing effect given by the saccharide derivatives of α,α-trehalose, it has a satisfactory skin feeling without sticky feeling when applied on skins.

A cleansing foam was prepared in the same manner to Example 41 except for using five parts by weight of sorbitol, as an ingredient of usual cleansing foams, instead of five parts by weight of saccharide derivatives of α,α-trehalose. The cleansing foam prepared above and the cleansing foam containing saccharide derivatives of α,α-trehalose, prepared in Example 40, were compared in view of bubble height of just after bubbling and five minutes later from bubbling according to Ross Miles method. The result is shown in Table 16.

TABLE 16

| Cleansing foam | Height of bubble (mm) | |
|---|---|---|
| | Just after bubbling | Five minutes after bubbling |
| Containing 7% of the syrup containing saccharide derivatives of α,α-trehalose | 198 | 171 |
| Containing 7% sorbitol | 186 | 160 |

As evidence from the result shown in Table 16, the cleansing foam containing the saccharide derivatives of α,α-trehalose showed higher bubble height of both of just after bubbling and five minutes later than the cleansing foam containing sorbitol. In addition, the former was also superior in view of the production and retain of bubble. The result reveals that saccharide mixture containing saccharide derivatives of α,α-trehalose more imparts elasticity to bubble of cleansing foams than sorbitol and is capable of improving the property of bubble.

Example 42

Shampoo

Thirty five parts by weight of 30% 2-alkyl-N-carboxymethyl-N-hydroxymethyl imidazolium betaine aqueous solution, 35 parts by weight of 30% triethanolamine cocoylglutamate aqueous solution, 10 parts by weight of the syrup containing saccharide derivatives of α,α-trehalose, prepared in Example 6, 10 parts by weight of 30% potassium cocoylglycine aqueous solution, 2.3 parts by weight of diethanolamide cocoate, three parts by weight of "αG HESPERIDIN", a glycosyl hesperidin commercialized by Hayashibara Biochemical Laboratories, Inc., Okayama, Japan, 0.005 part by weight of Kanko-so No. 201, 0.005 parts by weight of Kanko-so No. 301, and 10 parts by weight of purified water were mixed together, heat-dissolved to 70° C. with stirring, and admixed with an appropriate amount of perfumeries in a usual manner to obtain a shampoo. The product, enhanced in the blood flow-promoting effect of glycyrrhizinic acid by the saccharide derivatives of α,α-trehalose, is advantageously used for preventing itch of head skins, production of scurf, hair growing, hair nourishing, and treating and preventing aging of skins. Since the product has a satisfactory moisturizing effect given by the saccharide derivatives of α,α-trehalose in spite of without glycerin, it is a shampoo having a satisfactory skin feeling without sticky feeling.

Example 43

Hair Conditioner 2.5 parts by weight of liquid paraffin, 0.5 parts by weight of myristic acid, 1.5 parts by weight of cetanol, three parts by weight of glycerin monostearate, one part by weight of di-polyoxyethylene 2-octyldodecyl N-lauroyl glutamate and 0.5 part by weight of polyoxyethylene glyceryl monopyroglutamate monoisostearate were heated and mixed together. The resulting mixture was admixed with three parts by weight of the syrup containing saccharide derivatives of α,α-trehalose, prepared in Example 6, three parts by weight of 1,3-butylene glycol, 0.01 part by weight of Kanko-so No. 301, 2.5 parts by weight of lauroyl-L-lysine, 0.5 part by weight of fatty acid L-arginine ethylpyrolydon carbonate, 0.5 part by weight of stearyl trimethyl ammonium chloride, 0.1 part by weight of "αG RUTIN", a glycosyl rutin commercialized by Hayashibara Biochemical Laboratories, Inc., Okayama, Japan, one part by weight of sodium pyrrolidone carbonate, one part by weight of sialid extract, and 74 parts by weight of purified water with heating, and emusified in a usual manner to obtain a hair conditioner. The product, enhanced in the blood flow-promoting effect of sialid extract by the saccharide derivatives of α,α-trehalose, is advantageously used for preventing itch of head skins, production of scurf, hair growing, hair nourishing, and treating and preventing aging of skins. Since the product has a satisfactory moisturizing effect given by the saccharide derivatives of α,α-trehalose in spite of without glycerin, it is a hair conditioner having a satisfactory skin feeling without sticky feeling.

Example 44

Hair Treatment

Five parts by weight of stearyl alcohol, five parts by weight of glycerin monostearate, 3.5 parts by weight of liquid paraffin, two parts by weight of di-polyoxyethylene 2-octyldodecyl N-lauroyl glutamate and one part by weight of polyoxyethylene glyceryl monopyroglutamate monoisostearate were heated and mixed together. The resulting mixture was admixed with five parts by weight of the syrup containing saccharide derivatives of α,α-trehalose, prepared in Example 6, three parts by weight of 1,3-butylene glycol, one part by weight of stearyltrimethylammonium chloride, one part by weight of sodium pyrrolidone carbonate, 0.1 part by weight of dl-tocopherol, 0.1 part by weight of keratin polymer, and 65 parts by weight of deionized water with heating, and emulsified in a usual manner to obtain a hair treatment. The product, enhanced in the blood flow-promoting effect of dl-tocopherol by the saccharide derivatives of α,α-trehalose, is advantageously used for preventing itch of head skins, production of scurf, hair growing, hair nourishing, and treating and preventing aging of skins. Since the product has a satisfactory moisturizing effect given by the saccharide derivatives of α,α-trehalose in spite of without glycerin, it is a hair treatment having a satisfactory skin feeling without sticky feeling.

Example 45

Body Soap

Fifteen parts by weight of potassium laurate, 5.0 parts by weight of potassium myristate, 4.0 parts by weight of the syrup containing saccharide derivatives of α,α-trehalose, prepared in Example 6, 2.0 parts by weight of propylene glycol, 1.0 part by weight of chamomile extract, 0.5 part by weight of polyethylene powder, 0.5 part by weight of hydroxypropyl chitosan solution, 0.25 part by weight of glycine, 0.25 part by weight of glutamine, 0.2 part by weight of azulene, 0.1 part by weight of Kanko-so No. 201; an appropriate amount of pH-controlling agent and lavender water. The resulting mixture was admixed with purified water to give a final weight of 100 parts and emulsified in a usual manner in order to body soap. The product, enhanced in the antiinflammatory effect of azulene by the saccharide derivatives of α,α-trehalose, is advantageously used for preventing itch of skins, and treating or preventing aging of skins. Since the product has a satisfactory moisturizing effect given by the saccharide derivatives of α,α-trehalose in spite of without glycerin, it is a body soap having a satisfactory skin feeling without sticky feeling.

Example 46

Cleansing Oil 20.0 parts by weight of jojoba oil, 15.0 parts by weight of macadamia nut oil, 15.0 parts by weight of liquid paraffin, 9.0 parts by weight of cetyl isooctanoate, 20.0 parts by weight of POE(20) glycerin triisostearate, 10.0 parts by weight of POE (20) glycerin monoisostearate, 10.0 parts by weight of purified water, 0.1 part by weight of vitamin E and 1.0 part by weight of the powder containing saccharide derivatives of α,α-trehalose were mixed in a usual manner to obtain a cleansing oil. The product, enhanced in the antiinflammatory effect and/or blood flow-promoting effect of vitamin E by the saccharide derivatives of α,α-trehalose, has effects on preventing itch of skins, and treating and preventing aging of skins as well as cleansing effect. Therefore, it is advantageously used as a cosmetic for massage and bath oil. Since the product has a satisfactory moisturizing effect and a low stimulation against skins given by the saccharide derivatives of α,α-trehalose, it is a cleansing oil having a satisfactory skin feeling without sticky feeling. In addition, the product, improved in the stability of unsaturated fatty acids during preservation, has an advantage to suppress the generation of foreign odor and discoloration.

Example 47

Cleansing Powder

Forty six parts by weight of a powder containing saccharide derivatives of α,α-trehalose, produced by spray-drying the syrup prepared in Example 6 in a usual manner, 40 parts by weight of glucose, seven parts by weight of carboxy methylcellulose, one part by weight of "BIOECOLIA", a maltose-sucrose condensate commercialized by Nikko Chemicals, Co., Ltd., Tokyo, Japan, one part by weight of "AA2G®", an L-ascorbic acid 2-glucoside commercialized by Hayashibara Biochemical Laboratories, Inc., Okayama, Japan, 0.1 part by weight of allantoin, 0.2 part by weight of the powder prepared above in this Example containing 1,000 units/g of "LIPASE MY-30", a lipase (30,000 units/g) commercialized by Meito Sangyo Co., Ltd., Aichi, Japan, 0.002 part by weight of Kanko-so No. 401 and one part by weight of the powder prepared above in this Example above containing 5 units/g of "BIOPRASE CONC", a protease (150,000 units/g) commercialized by Nagase Chemtex Corporation, Osaka, Japan, were mixed together, and passed through a 26-mesh sieve to homogeniety to obtain a powdery product. The product, enhanced in the antiphlogistic effect of allantoin by the saccharide derivatives of α,α-trehalose, has effects on preventing itch of skins, and treating and preventing aging of skins as well as it is effective on removing excessive sebum and old keratin from facial skins. Therefore, it is advantageously used for preventing stimulation or itch of skins, and treating or preventing aging of skins. Since the product has a satisfactory moisturizing effect given by the saccharide derivatives of α,α-trehalose in spite of without glycerin, it is a cleansing powder having a satisfactory skin feeling without tightening feeling after applied.

Example 48

Mouse Wash

Fifteen parts by weight of ethanol, 10 parts by weight of the syrup containing saccharide derivatives of α,α-trehalose, prepared in Example 1, one part by weight of "αG HESPERIDIN", a glycosyl hesperidin commercialized by Hayashibara Biochemical Laboratories, Inc., Okayama, Japan, two parts by weight of polyoxyethylene caster wax, 0.02 part by weight of saccharine-Na, 0.05 part by weight of sodium benzoate, 0.1 part by weight of sodium dihydrogenphosphate, appropriate amount of colorants and perfumeries, and 72.2 parts by weight of water were mixed together to obtain a mouth wash. The product, enhanced in the blood flow-promoting effect of glycosyl hesperidin by the saccharide derivatives of α,α-trehalose, has effects on improving dry mouth due to Sjogren syndrome, and preventing or treating oral inflammations and dysgeusia. In addition, it is a mouth wash having a satisfactory skin feeling.

Example 49

Toothpaste

Thirty parts by weight of dipotassium hydrogen phosphate, 10 parts by weight of hydroxyapatite, five parts by weight of calcium carbonate, 30 parts by weight of the syrup containing saccharide derivatives of α,α-trehalose, prepared in Example 1, 1.5 parts by weight of sodium rauryl sulfate, 0.7 part by weight of sodium monofluorophosphate, 0.5 part by weight of polyoxyethylene sorbitan raurate, 0.5 part by weight of diphenhydramine hydrochloride, 0.05 part by weight of antiseptics, 22 parts by weight of purifies water were mixed together to obtain a toothpaste. The product, enhanced in the blood flow-promoting effect of diphenhydramine hydrochloride by the saccharide derivatives of α,α-trehalose, has effects on preventing or treating oral inflammations and dysgeusia, or swelling, inflammation and bleeding of teethridge due to alveolar pyorrhea. In addition, it is a toothpaste having a satisfactory skin feeling.

Example 50

Toothpaste

Thirty parts by weight of dipotassium hydrogen phosphate, 10 parts by weight of hydroxyapatite, five parts by weight of calcium carbonate, 30 parts by weight of the syrup containing saccharide derivatives of α,α-trehalose, prepared in Example 1, 2.0 parts by weight of propolis extract, 1.5 parts by weight of sodium rauryl sulfate, 1.5 parts by weight of glycyrrhiza extract, 1.0 part by weight of "αG HESPERIDIN", a glycosyl hesperidin commercialized by Hayashibara Biochemical Laboratories, Inc., Okayama, Japan, 0.7 part by weight of sodium monofluorophosphate, 0.5 part by weight of polyoxyethylene sorbitan raurate, 0.5 part by weight of antiseptics, 19 parts by weight of purifies water were mixed together to obtain a toothpaste. The product, enhanced in the antiinflammatory effect of glycyrrhizia extract and the blood flow-promoting effect of glycosyl hesperidin by the saccharide derivatives of α,α-trehalose, which are non-cariogenetic saccharides and hardly produce water-insoluble glucans with acidic fermentation and has an anticarious effect on inhibiting the production of water-insoluble glucans from sucrose, has effects on preventing dental caries, and preventing or treating oral inflammations and dysgeusia, or swelling, inflammation and bleeding of teethridge due to alveolar pyorrhea. In addition, it is a toothpaste having a satisfactory skin feeling.

Example 51

Kitchen Detergent

Twenty one parts by weight of a surfactant composition consisting of sodium alkylalanine methylalanine alkylamidepropylbetaine and fatty acid diethanolamide, five parts by weight of the powder containing saccharide derivatives of α,α-trehalose, prepared in Example 7, 0.1 part by weight of vitamin E, and appropriate amounts of polyoxyethylene alkyl ether, perfumeries and colorants were mixed together to obtain a kitchen detergent. The product, having a strong detergency and enhanced in the antiphlogistic effect of vitamin E by the saccharide derivatives of α,α-trehalose, has an effect on preventing rough skins due to using detergents. The product has not only satisfactory moisturizing effect, but also it is capable of suppressing in the defatting due to surfactants, denaturation of corneous proteins, and permeability of skins by an skin protecting effect of saccharide derivatives of α,α-trehalose therein. The product is a kitchen detergent having an inhibitory effect on skin disorders such as rough skins of hands, etc., and a satisfactory skin feeling without tightening feeling after applied. In addition, the product can be advantageously used for alleviating pains or disorders due to insect bite and sting, or contacting to a kind of poisonous moth or larva thereof in a manner of applied on the skins.

Example 52

Ointment for Treating External Injuries 450 parts by weight of macrogol (400), three parts by weight of carboxyvinylpolymer, one part by weight of pullulan, 400 parts by weight of isopropanol, one part by weight of chlorhexidine gluconate solution and 10 parts by weight of indomethacin were mixed in vacuo. The resulting mixture was admixed with 70 parts by weight of the powder containing saccharide derivatives of α,α-trehalose, prepared in Example 3, three parts by weight of sodium hydroxide and 77 parts by weight of purified water to obtain a ointment for treating external injuries with an appropriate extension and adherence. The product, enhanced in the antiinflammatory effect of indomethacin by the saccharide derivatives of α,α-trehalose, is capable of treating external injuries accompanying itches and pains of cuts, grazes, burns, athlete's foot or frostbites in a manner of applying directly or with a gauze to such a wounded surface. The product, containing saccharide derivatives of α,α-trehalose, is an ointment for treating external injuries having a satisfactory skin feeling without sticky feeling.

INDUSTRIAL APPLICABILITY

The external dermatological formulation of the present invention contains safe and extremely stable saccharide derivatives of α,α-trehalose and a substance having any one of blood flow-promoting effect, antiinflammatory effect, antibacterial effect, moisturizing effect, whitening effect, UV-absorbing effect, UV-scattering effect, antioxidant effect, hairing effect, hair nourishing effect, astringent effect, wrinkle-reducing effect, cell-activating effect and transdermal absorption-promoting effect as effective ingredients. The formulation has a satisfactory skin feeling without sticky feeling, and is enhanced in the effects of effective ingredients by saccharide derivatives of α,α-trehalose. Therefore, it is used in the various fields such as cosmetics, quasi-drugs, pharmaceuticals and gloceries.

The present invention with such as outstanding function and effect is a significant invention that will greatly contribute to this art.

The invention claimed is:

1. An external dermatological formulation adapted for application to skin, wherein the formulation comprises (A) a saccharide composition, which saccharide composition comprises, on a dry solid basis, (1) 50 to 70% of α-maltosyl α,α-trehalose, (2) 5 to 25% of total other saccharide derivatives of α,α-trehalose, and (3) 25 to 45% of sugar alcohols selected from the group consisting of sorbitol and sugar alcohols of maltooligosaccharides, (B) hyaluronic acid in a moisturizing effective amount, and (C) an amount sufficient to promote blood flow of sialid extract, whereby the external dermatological formulation has improved blood flow promoting effect of the sialid extract.

2. A process for making the external dermatological formulation of claim 1, which comprises incorporating said saccharide composition in an external dermatological formulation containing hyarulonic acid and sialid extract.

3. The external dermatological composition according to claim 1, wherein the saccharide composition is present in an amount of from 0.001 to 50% of the total dermatological compositions.

4. The external dermatological composition according to claim 3, wherein the saccharide composition is present in an amount of from 0.1 to 40% of the total dermatological composition.

* * * * *